US005473056A

United States Patent [19]
Ivey-Hoyle et al.

[11] Patent Number: 5,473,056
[45] Date of Patent: Dec. 5, 1995

[54] E2F-2, A NOVEL MAMMALIAN TRANSCRIPTION FACTOR

[75] Inventors: Mona Ivey-Hoyle, King of Prussia; Allen I. Oliff, Gwynedd Valley, both of Pa.; David C. Heimbrook, Ringoes, N.J.

[73] Assignee: Merck & Co., Inc., Rahway, N.J.

[21] Appl. No.: 136,119

[22] Filed: Oct. 13, 1993

[51] Int. Cl.$^6$ ................................................. C07K 14/47
[52] U.S. Cl. ........................................ 530/358; 536/23.5
[58] Field of Search ............................... 435/69.1, 172.1, 435/172.3, 252.33, 320.1, 254.2, 254.21, 254.11, 252.31, 252.34, 252.35, 252.3; 530/350, 358; 536/23.5

[56] References Cited

FOREIGN PATENT DOCUMENTS

92/12728  8/1992  WIPO ............................ C12N 15/37

OTHER PUBLICATIONS

Gould et al. (1989), PNAS USA 86, 1934–1938.
Helfman et al. (1987) in "Method in Enzymol., V. 152" pp. 451–457, Academic Pr., N.Y.
Girling et al. (1993). Nature 362, 83–87.
Nevins (1992). Science 258, 424–429.
Bagchi, S. et al., The Retinoblastoma Protein Copurifies with E2F–1, an E1A–Regulated Inhibitor of the Transcription Factor E2F, (1991), Cell, 65, pp. 1063–1072.
Bandara, L. R. et al., Cyclin A and the retinoblastoma gene product complex with a common transcription factor, (1991), Nature, 352, pp. 249–251.
Blake, M. C. et al., Transcription Factor E2F Is Required for Efficient Expression of the Hamster Dihydrofolate Reductase Gene in Vitro and In Vivo, (1989), Mol. & Cell Biol., 9, pp. 4994–5003
Chellappan, S. P. et al., The E2F Transcription Factor Is a Cellular Target for the RB Protein, (1991), Cell, 65, pp. 1053–1061.
Cao, L. et al., Independent binding of the retinoblastoma protein and p107 to the transcription factor E2F, (1992), Nature, 355, pp. 176–179.
DeFeo–Jones, D. et al., Cloning of cDNAs for cellular proteins that bind to the retinoblastoma gene product, (1991), Nature, 352, pp. 251–254.
DeFeo–Jones, D. et al., Papillomavirus E7 Protein Binding to the Retinoblastoma Protein is Not Required for Viral Induction of Warts, (1993), Jour. of Virol., 67, pp. 716–725.
Devoto, S. H. et al., A Cyclin A–Protein Kinase Complex Possesses Sequence–Specific DNA Binding Activity: p33cdk2 is a Component of the E2F–Cyclin A Complex, (1992), Cell, 68, pp. 167–176.
Eisenberg, S. P. et al., Primary structure and functional expression from complementary DNA of a human interleukin–1 receptor antagonist, (1990), Nature, 343, pp. 341–346.
Girling, R. et al., A new component of the transcription factor DRTF1/E2F, (1993), Nature, 362, pp. 83–87.
Hiebert, S. W. et al., E1A–dependent trans–activation of the human MYC promoter is mediated by the E2F factor, (1989), Proc. Natl. Acad. Sci. USA, Biochemistry, 86, pp. 3594–3598.
Hiebert, S. W. et al., Role of E2F Transcription Factor in E1A–Mediated trans Activation of Cellular Genes, (1991), Jour. of Virol., 65, pp. 3547–3552.
Hiebert, S. W. et al., The interaction of RB with E2F coincides with an inhibition of the transcriptional activity of E2F, (1992), Genes & Development, 6, pp. 177–185.
Helin, K et al. et al., A cDNA Encoding a pRB–Binding Protein with Properties of the Transcription Factor E2F, (1992), Cell, 70, pp. 337–350.
Huber, H. E. et al., Transcription factor E2F binds DNA as a heterodimer, (1993), Proc. Natl. Acad. Sci. USA, Biochemistry, 90, pp. 3525–3529.
Huang, P. S. et al., Protein Domains Governing Interactions between E2F, the Retinoblastoma Gene Product, and Human Papillomavirus Type 16 E7 Protein, (1993), Mol. and Cell. Biol., 13, pp. 953–960.
Kaelin, W. G. et al., Expression Cloning of a cDNA Encoding a Retinoblastoma–Binding Protein with E2F–like Properties, (1992), Cell, 70, pp. 351–364.
Mudryj, M. et al., Cell Cycle Regulation of the E2F Transcription Factor Involves an Interaction with Cyclin A, (1991), Cell, 65, pp. 1243–1253.
Nevin, J. R., E2F: A Link Between the Rb Tumor Suppressor Protein and Viral Oncoproteins, (1992), Science, 258, pp. 424–429.
Shan, B. et al., Molecular Cloning of Cellular Genes Encoding Retinoblastoma–Associated Proteins: Identification of a Gene With Properties of the Transcription Factor E2F, (1992), Molec. and Cellular Biol., 12, pp. 5620–5631.
Shirodkar, S. et al., The Transcription Factor E2F Interacts with the Retinoblastoma Product and a p107–Cyclin A Complex in a Cell Cycle–Regulated Manner, (1992), Cell, 68, pp. 157–166.
Stammer, D. K. et al., Rapid purification and characterisation of HIV–1 reverse transcriptase and RNaseH engineered to incorporate a C–terminal tripeptide α–tubulin epitope, (1991), FEBS, 283, pp. 298–302.
Thalmeier, K. et al., Nuclear factor E2F mediates basic transcription and trans–activation by E1a of the human MYC promoter, (1989), Genes & Development, 3, pp. 527–536.
Weintraub, S. J. et al., Retinoblastoma protein switches the E2F site from positive to negative element, (1992), Nature, 358, pp. 259–261.

*Primary Examiner*—Mindy B. Fleisher
*Assistant Examiner*—James Ketter
*Attorney, Agent, or Firm*—David A. Muthard; Mark R. Daniel

[57] ABSTRACT

The present invention is directed to a novel protein with E2F-like properties and the cDNA that encodes for that protein. The purified protein exhibits biological activity which is deemed important to medical science in the study of cell cycle regulation in general and the specific study of the Rb rumor suppressor protein and certain viral oncogenes. The protein may be employed in a complex with pRb or other cellular proteins to study inhibitors of biochemical transformations of those proteins, such as for example the phosphorylation of the pRb portion of the complex, therefore aiding in the study of potential pharmaceutical agents useful against certain oncoproteins encoded by DNA tumor viruses.

2 Claims, 9 Drawing Sheets

```
1201  TTGGCAACTTTAAGGAGCAGACAGTGATTGCCCTCAAGCCCTCCCAGACAGCCCCTGAGGACAACTGAGATGCCCACAGGACTGAGGACAACTGAGATATCTCAAGACACCCAAGGCCCA
       G N F K E Q T V I A V K A P P Q T R L E V P D R T E D N L Q I Y L K S T Q G P I (298)
1321  TCGAAGTCTACCTGTGCCCAGAGGAGTGCAGGAGCCCGACAGTCCTTCCGAGGAGCCCTCTCCACCCTCTACCTCCACCCTGACTCTGCCCAGCCAGCAGCACCG
       E V Y L C P E E V Q E P D S P S E E P L P S T S T L C P S P D S A Q P S S T D (338)
1441  ACCCTAGCATCATGGAGCCCACAGATCCTCAGTGCCAGCCACACAGCCTCCATCCTGGTCCCCTTGGAGCTACTGACAGCCTGCTGGAGCTGC
       P S I M E P T A S S V P A P T P Q Q A P P P S L V P L E A T D S L L E L P (378)
1561  CGCACCCACTCCTGCAGCAGACTGAGGACAGTCCTGTCCCCGACCCTGGCTGCAGCTCCTCTGATCAGCTTCTCCCCATCCTTGGACCAGGACGACTACCTGTGGGGCTTGGAGG
       H P L L Q T E D Q F L S P T L A C S S P L I S F S P S L D Q D D Y L W G L E A (418)
1681  CGGGTGAGGGCTACACGGATCTCTTGCACTCTTGCAGACCTTGGGGACCTTGATTAATTGATGCCCCTGCCCTGCCCCCAGCACCCTGCCCCGACTCCTACCTCCTCACACAGGCTG
       G E G I S D L F D S Y D L G D L L I N *
1801  ACAGCCCCTCTGCCTGCACAGGGACATTGGACACTAGGTGCTGCCCTCAGGCATGGGTCTCGCTCTCCCTTTCCTGCCCAGCCGGCAGA AGCTGTGTGGGGAGATATGAATGGTACGGG
1921  TGAGGAGTGGATAAGGGTGGTCCTCACCTTCCTAATGGACTCGGCCTAGGCAGGAGCCCATCCAGTCTCTGACTCTGACTCTCACAAGA AGGCTGCAGGTGAGGTGCCAAGTCCA
2041  GGGAAAGGCCCTGCTACCTCCTTTTGAGGGTAATTAGGACCCTGACGTAGCAAAGAAGCACATAATGCCTTTGTATTTATTTCAGGTTG AGTTGTTTGTCTCCCTGAGTTTTAG
2161  CAGGGAGGTGTTCTAGTTTTTAGTGACCTCTGAGGCTGTCTCCAGTCTCTGCAGACAGCCCATCAGGCCTCCATGTTCCAGGGAGGGCCC AGCTACATCCTTGGTTTCCCCACT
2281  GTGGTGGGGCTCTGGGACTCTGGAGCTGCCGGTCTTGGCTCTGCCTCGTGGCTCCAGTGTTCTAGTAAACGGCACTGTG GGGCCTTTGCCTCTTCCCGTTCTTGGC
2401  CTCACATCCACCTGAGCTGCCGGTCCTGAGCTGCCACTGAGCTTCCTCGTCCAGGGAGGACCATCCTGTCCAGGCAGTGTCCCAGGCAGTAGCACTGAGGC TCCTGTGAAACAGAGCCACCT
2521  GCTCAGGAGACCCCTTTCCTGAGGAAGTCCTTACCTCTCCCCTTGAGATGTAAAAATGGTCCAGCAGCAAGCTCCCGTGAAAAACAG ACAGGAGCATGGGGCAGCTGTCATGGCTG
2641  TGGCGGG
```

```
              1          20          40          60          80    86
              |          |           |           |           |     |
E2F-2:  MLQGPRRALASAAGQTPKVVPAMSPTELWPSGLSSPQLCPATATYYTPLYPQTAPPAAAPGTC.....LDATPHGPEGQVVRCLPA.GRLPAK
                     |||||||| || |   || | ||  ||   |    |  |    ||  ||||||  ||| ||||
E2F-1:  ..MALAGAPAGGPCAPALEALLGAGALRLLDSSQIVIISAAQDASAPPAPTGPAAPAAGPCDPDLLLFATPQAPRPTPSAPRPALGRPPVK
        1         16          36          56                    82          89

87                 112      132  :           152 :   172 :           193          209
        |                  |        |                |       |               |            |
RKLDLEG IGRPVVPEFPTPKGKCIRVDGLPSPKTPKSPGEKTRYDTSLGLLTKKFIYLSESEDGVLDLNMAAEVLDVQKRRIYDITNVLEGIQLIRKKAKNNIQMVGRGMFEDPTRPGKQQQ
|||||   |    |           |||  | |||  |||||||||||||||||||||| |||||||| ||||||||||||||||||||||||||||||||||||||||  ||||||||
RRLDLET.DHQYLAESSGP.....ARGRGRHPGKGVKSPGEKSRYETSLNLTTKRFLELLSHSADGVVDLNMAAEVLKVQKRRIYDITNVLEGIQLIAKKSKNHIQWLGS..HTIVGVGGRLEG
90            102           120       130           150     170             191          205

210              230              250              270              290             310         332
    |                |                |                |                |               |           |
LGQELKELMNTEQALDQLIQSCSLSFKHLTEDKANKRLAYVITYQDIRAVQNFKEQTVIAVKAPPQTRLEVPDRTEDNLQIYLKSTQGPIEVYLCPEEVQEPDSPSEEPLPSTSTLCPSPDSAQ
| || || |  | | ||||||| ||||||||||||||| |  ||| ||||||||||||  |||||||||| ||   |||||  |  |||||||  ||||  ||   |||||||||  || |
LTQDLRQLRQLQESEQQLDHLMNICTTQLRLLSEDTDSQRLAYVTCQDLRSIADPAEQMVMVIKAPPETQLQAVDSSE.NFQISLKSKQGPIDVFLCPEETVGGISPGKTP......SQEVTSEE
206               226              246              266              285            305         320

333              353              373              393           410          427       437
    |                |                |                |             |            |         |
PSSSTD.PSIMEPTASSVPAPAPTPQQAPPPPSLVPLEATDSLLELPHPLLQQTEDQFLSPTLACSS..........PLISFSPSLDQDDYL.WGLEAEGEISDLFDSYDLGDLLIN..
|||  | |||  || |   |||| ||    ||| ||| ||||| ||   |  ||||| ||       || ||| ||| ||    ||  ||  |||| |||||| |||||||||| |
ENRAIDSATIVSPPPSSPPSSLTT....DPSQSLLSLEQ.EPLLSRMGSLRAPVDEDRLSPLVAADSLLEHVREDFSGLLPEEFISLSPPHEALDYH.FGLEEEGIRDLFD.CDFGDLTPLDF
321               342              357              377          409         426       437
```

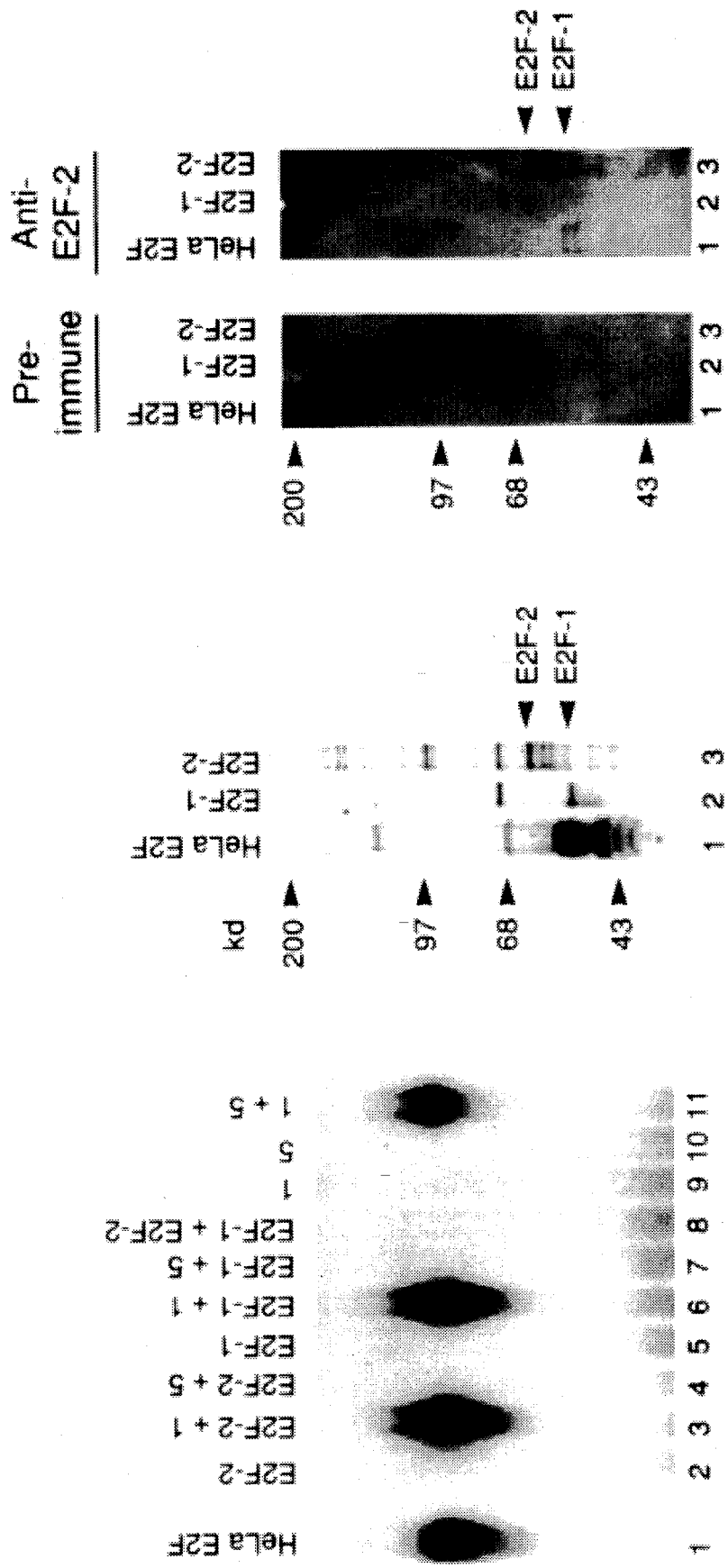

E2F-2, A NOVEL MAMMALIAN TRANSCRIPTION FACTOR

BACKGROUND OF THE INVENTION

This invention relates to a novel protein and, more particularly, to a highly purified mammalian transcription factor given the name E2F-2.

The mammalian transcription factor E2F was originally identified as a cellular factor recruited by adenovirus Type 5 to initiate transcription from the viral E2 promoter (for a review see J. R. Nevins, *Science,* 258:424–429 1992)). It has subsequently been suggested that E2F may play a critical role in cell-cycle regulation of uninfected mammalian cells, as well. E2F binding sites are found in the promoter regions of several cellular genes which are important for cell growth, including c-myc, cdc2, and DHFR. E2F activity appears to be regulated via complex formation with other cellular proteins in a cell-cycle dependent fashion. Binding of E2F to the retinoblastoma gene product (pRb) yields a complex which suppresses transcription of genes containing the E2F binding site. Only the underphosphorylated form of pRb is found in the E2F/pRb complex, and the complex is present in the $G_1$ stage of the cell cycle and persists into the S phase. Interactions of E2F with other cellular proteins, including the pRb homolog p107 and cyclins, suggest that a complicated set of growth regulatory functions are mediated by these proteins.

Clones of two distinct proteins with E2F-like activity have recently been identified. Human E2F-1 was identified by probing expression libraries with recombinant pRb (W. J. Kaelin et al., *Cell,* 70:351–364 (1992); B. Shan et al., *Mol. Cell. Biol.,* 12:5620–5631 (1992); K. Helin et al., *Cell,* 70:337–350 (1992)). This protein displays many of the properties of authentic E2F, including binding to the E2F recognition element in a sequence-specific fashion and binding to pRb. Furthermore it has been shown that the DNA and pRb binding activities of purified HeLa cell E2F and recombinant E2F-1 are enhanced by heterodimerization (H. E. Huber et al., *Proc. Natl. Acad. Sci. USA,* 90:3525–3529 (1993)). Following preparative SDS-PAGE of affinity-purified E2F, two sets of proteins were identified, and one component from each set was required for optimal reconstitution of activity. It has also been demonstrated that recombinant E2F-1 forms homodimers, and proposed that these homodimers may be responsible for the observed DNA and pRb binding activity of E2F-1 in the absence of its normal partner. A distinct protein (DP-1) was more recently cloned based on amino acid sequence data obtained from E2F purified from mouse F9 cells (R. Girling et al., *Nature,* 363:83–87 (1993)). This cloned protein also displays the key biochemical properties of cellular E2F, but displays little sequence homology to E2F-1 outside of the DNA binding domain.

Isolation, purification, identification and expression of proteins having E2F-like activity is useful in studying the mechanisms of cell proliferation and for screening for compounds which would inhibit such activity and, consequently, inhibit abnormal cell proliferation.

BRIEF DESCRIPTION OF THE FIGURES

FIG. 1. E2F-2 amino acid sequence and cDNA encoding sequence The nucleotide sequence which encodes E2F-2 is shown along with the corresponding amino acids of E2F-2 which are provided undeneath the cDNA sequence. (cDNA: SEQ.ID.NO.: 1; amino acid: SEQ.ID.NO.: 2)

FIG. 3. Sequence of clones from λgt11 library Nucleotide sequence obtained from clones 9 (1–1766; end indicated by "#") and 10 (685–2647). The amino acid sequence of the longest open reading frame (437 aa) is provided underneath the corresponding nucleotides. The initiating Met codon and the stop codon are boxed. The 5' in-frame stop codon is undefined. (cDNA: SEQ.ID.NO.: 3; amino acid: SEQ.ID.NO.: 2)

FIG. 4. Amino acid sequence comparison of E2F-2 and E2F-1 Amino acid sequence comparison of E2F-2 and E2F-1, generated by the "Gap" subroutine of GCG. Several conserved features are marked as follows: helices of the helix-loop-helix domain (a.a. 130–144 and 158–183) are boxed with a solid line; conserved hydrophobic residues within these helices are denoted with a "*"; basic residues within the DNA binding region are denoted with a "#"; conserved hydrophobic residues of the N-terminal and C-terminal zipper-like motifs are denoted with a "+" and a "‡", respectively; and the pRb binding domain (a.a. 410–427) is boxed with a dashed line. (E2F-2 amino acid: SEQ.ID.NO.: 2; E2F-1 amino acid: SEQ.ID.NO.: 4)

FIG. 8. E2F-2 dimerization studies Panel A—Affinity-purified E2F-2 (2 μg/ml) and E2F-1 (5 μg/ml) were refolded with protein eluted from band 1 (lanes 3, 6) or band 5 (lanes 4, 7) of SDS-PAGE-purified HeLa cell E2F as described by H. E. Huber et al. (*Proc. Natl. Acad. Sci. U.S.A.,* supra) and assayed in the gel shift assay. An excess of unlabeled DNA containing mutant E2F binding site was added to each sample to eliminate non-specific binding. Lane 1 contains affinity-purified HeLa cell E2F. Bands 1 and 5 were also assayed individually (lanes 9 and 10, respectively) or after mixing and co-refolding (lane 11). Panel B—Silver stain of HeLa cell E2F and affinity purified E2F-1 and E2F-2 following SDS-PAGE. The prominent HeLa E2F bands at approximately 50 kDa are bands 1–3, and the darker bands at approximately 55 kDa (comigrating with *E. coli* E2F-1) are bands 4 and 5. Panel C—"Western" blot of the samples in Panel B using rabbit preimmune serum (left panel) or a rabbit anti-E2F-2 (196–210) antiserum (right panel).

DISCLOSURE OF THE INVENTION

Figure 1:
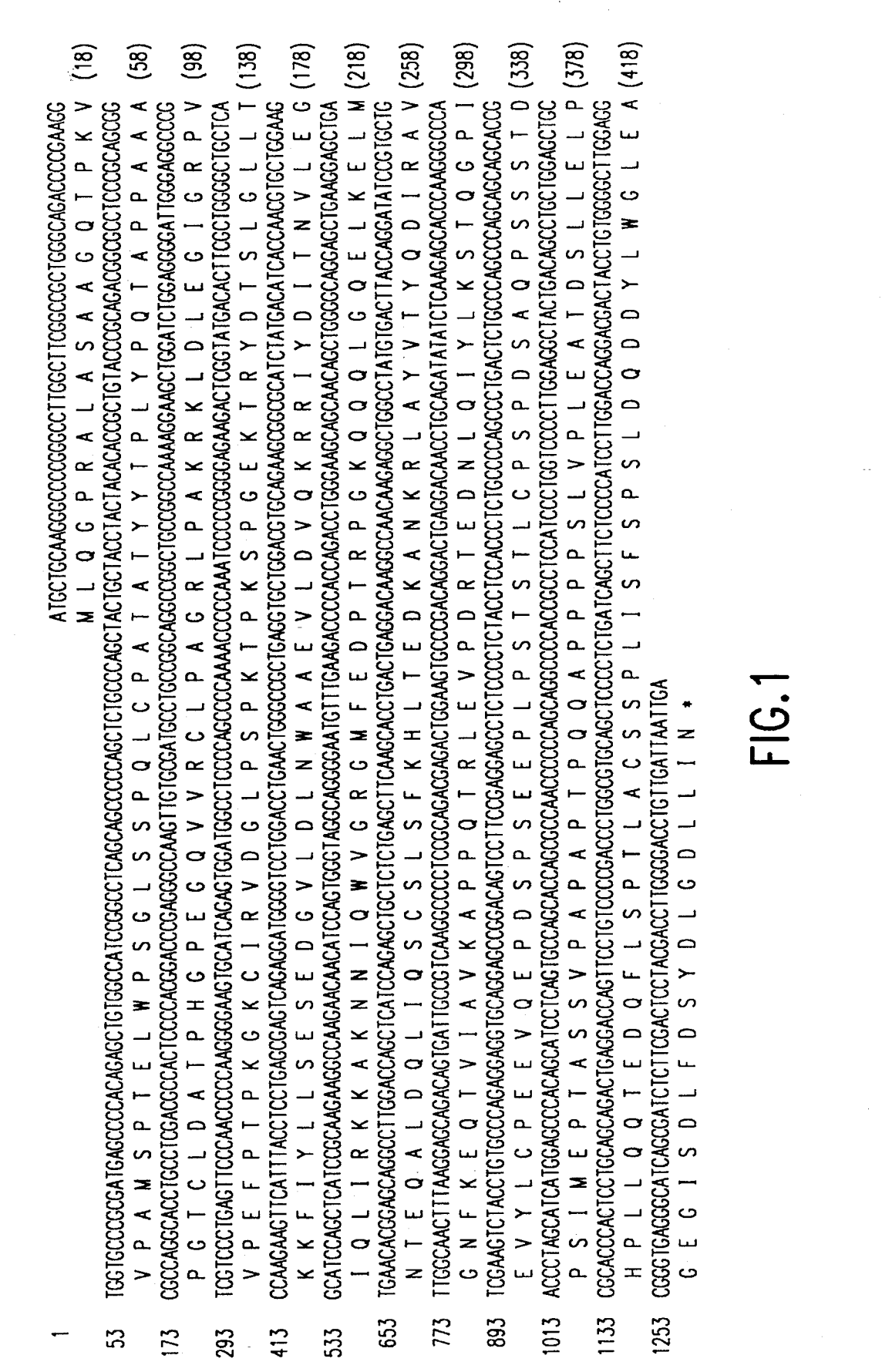
Figure 2A:
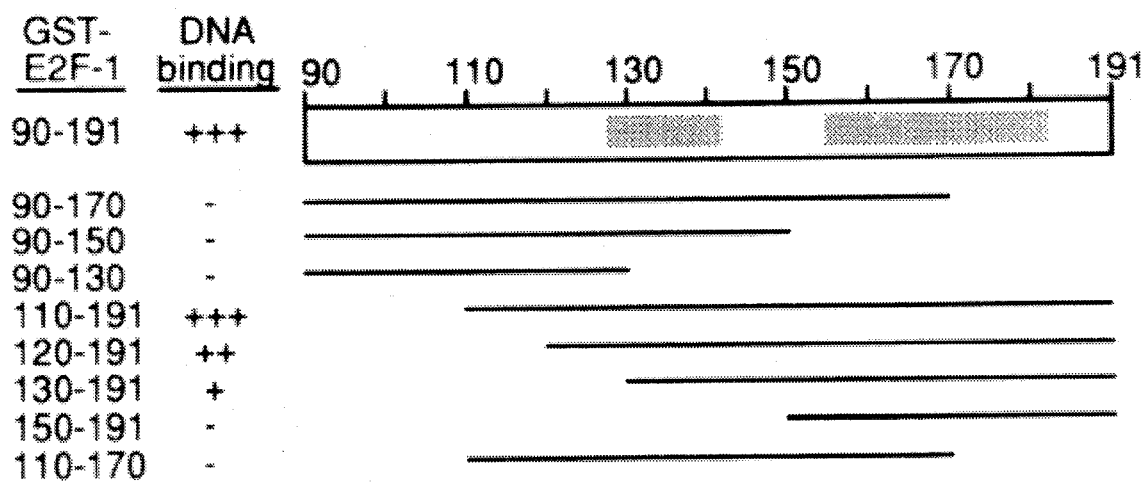
FIG. 2. Identification of the minimal DNA binding domain of E2F-1. GST-E2F-1 fusion proteins containing the indicated E2F-1 amino acids were tested for their ability to bind a radiolabled DNA sequence containing a single palindromic E2F binding site in the gel-shift assay. Fusion protein concentrations were normalized by "Western" blotting with an anti-GST antibody. Gel shift assay results are shown. Lane 1— no competitor. Lane 2—contains excess unlabeled mutated competitor DNA. Lane 3—contains excess unlabeled wild-type DNA.

This present invention relates to a novel protein with E2F-like properties having the amino acid sequence illustrated in FIG. 1 (SEQ.ID.NO.: 1).

The purified protein exhibits biological activity which is deemed important to medical science in the study of cell cycle regulation in general and the specific study of the Rb tumor suppressor protein and certain viral oncogenes. The protein may be employed alone or in a complex with pRb or other cellular proteins to study inhibitors of transcriptional activation or biochemical transformations of those proteins, such as for example the phosphorylation of the pRb portion of the complex, therefore aiding in the study of potential pharmaceutical agents useful against abnormal cellular proliferation or certain oncoproteins encoded by tumor viruses.

The present invention also relates to novel cDNA sequence which is illustrated in FIG. 1 (SEQ.ID.NO.: 2), which encodes the protein E2F-2.

Although particular methods of isolating the E2F-2 protein are described herein, it will be understood that the novel E2F-2 protein is not limited to any specific method of preparation.

Thus, the present invention is also concerned with particular techniques for the identification and isolation of E2F-2. For instance one method of preparing the E2F-2 protein includes the steps of:

(a) preparing a cellular extract which includes the protein; and (b) subjecting the extract to affinity chromatography by binding the protein to an affinity chromatography medium; washing the medium to remove impurities; and eluting the protein from the washed medium.

Thus, the first step of the purification protocol involves simply preparing a cellular extract which includes the protein. The inventors have discovered that the protein is soluble in buffers such as low-salt buffers, and it is proposed that virtually any buffer of this type can be employed for initial extraction of the protein from a tissue of choice. The inventors prefer a 50 mM Tris-chloride, pH 7.5, buffer which includes divalent chelator (e.g., 1 mM EDTA, 1 mM EGTA), as well as protease inhibitors such as PMSF and/or leupeptin. Of course, those of skill in the art will recognize that a variety of other types of tissue extractants may be employed where desired, so long as the protein is extractable in such a buffer and its subsequent activity is not adversely affected to a significant degree.

The type of tissue from which one will seek to obtain the E2F-2 protein is believed to be of importance. While E2F-2 protein may be a component of virtually all living cells, certain tissue has been shown to exhibit higher levels of mRNA expression. Therefore, the tissue of choice will typically be that which is most readily available to the practitioner which shows significant expression of the protein.

The protein may be isolated from human placenta in that this source is readily available. However, numerous other sources are contemplated to be directly applicable for isolation of the protein, including many immortalized cell lines derived from tumor samples. Those of skill in the art, in light of the present disclosure, should appreciate that the techniques disclosed herein will be generally applicable to all such E2F-2 sources.

After the cell extract is prepared the protein is preferably subjected to two partial purification steps prior to affinity chromatography. These steps comprise selective precipitation with ammonium sulfate, by first treating the cell extract with an ammonium sulfate solution which precipitates contaminating proteins but leaves the E2F-2 in the supernatant (for instance, 30% saturated ammonium sulfate). The supernatant is then treated with a more concentrated solution of ammonium sulfate (for instance, 50% saturated ammonium sulfate) which precipatates E2F-2 but leaves other contaminating proteins in the supernatant. The pelleted protein is then dissolved, preferably in a solution of 20 mM Tris-chloride (pH 7.5) containing 1 mM DTT and 20 µM $ZnCl_2$. After dialysis against the same buffer the protein solution is applied to an ion exchange column containing an ion exchange resin such as Mono Q. After washing of the column, the protein is eluted with a salt gradient (for instance 0.25M–1.0M NaCl) in the same buffer.

It is, of course, recognized that the preliminary purification steps described above are preferred laboratory procedures that might readily be replaced with other procedures of equivalent effect such as ion exchange chromatography on other resins or gel filtration chromatography. Indeed, it is possible that these steps could even be omitted and the crude cell extract might be carded directly to affinity chromatography.

After the preliminary purification steps, the extract may be subjected to affinity chromatography on an affinity chromatography medium which includes a oligonucleotide containing an E2F-2 binding site coupled to a suitable matrix.

The initial step in this process is binding the E2F-2 by passing the protein solution, in a suitable buffer, over an affinity matrix. The next step in the overall general purification scheme involves simply washing the medium to remove impurities. That is, after subjecting the extract to affinity chromatography on the affinity matrix, one will desire to wash the matrix in a manner that will remove the impurities while leaving the E2F-2 protein relatively intact on the medium. A variety of techniques are known in the art for washing matrices such as the one employed herein, and all such washing techniques are intended to be included within the scope of this invention. Of course, for washing purposes, one will not desire to employ buffers that will release or otherwise alter or denature the protein. Thus, one will typically want to employ buffers which do not contain high concentrations of denaturing detergents such as SDS buffers.

After the matrix-bound protein has been sufficiently washed, for example in a medium-ionic strength buffer at essentially neutral pH, the specifically bound material can be eluted from the column by using a similar buffer but of reduced pH (for example, a pH of between about 4 and 5.5). At this pH, the protein will typically be found to elute from the preferred affinity matrices disclosed in more detail hereinbelow. Typically the protein is eluted into a neutralizing buffer to prevent deleterious effects of the buffer having reduced pH.

While it is believed that advantages in accordance with the invention can be realized simply through affinity chromatography techniques, additional benefits will be achieved through the application of additional purification techniques, such as gel filtration techniques. For example, Sephacryl S-200 high resolution gel columns can be employed with significant benefit in terms of protein purification. However, the present disclosure is by no means limited to the use of Sephacryl S-200, and it is believed that virtually any type of gel filtration arrangement can be employed with some degree of benefit. For example, one may wish to use techniques such as gel filtration, employing media such as Superose, Agarose, or even Sephadex. In addition, since E2F-2 may form complexes with other protein components in cells (see below), preparative SDS-polyacrylamide gel electrophoresis may be useful for separating E2F-2 from these other cellular components. Individual protein bands are separated with a razor blade, electroeluted into 20 mM bicarbonate/0.01% SDS, and concentrated on a centrifugal filtration apparatus. Electroeluted protein samples are refolded by diluting them into a non-denaturing buffer.

Through the application of various of the foregoing approaches, E2F-2 protein compositions of relatively high purity may be achieved. For the purposes of the present invention purity may be assessed via SDS-polyacrylamide gel electrophoresis. The activity of the purified protein may be assessed via the gel shift assay described herinbelow and the ability of the protein to compete with wild type E2F in binding studies with pRb.

Once E2F-2 is purified to homogeneity, its amino acid sequence can be determined, in whole or part, using standard sequencing techniques, e.g., Edman degradation. (See, for example, Creighton, 1983, Proteins, Structures and Molecular Principles, W. H. Freeman and Co., New York, pp. 34–39). These amino acid sequences (whole or partial) may then be used to derive nucleotide coding sequences for E2F-2. These nucleotide sequences, or fragments or functional equivalents thereof, may be used to generate recombinant DNA molecules that direct the expression of the E2F-2 gene product, or functionally active peptides or functional equivalents thereof, in appropriate host cells.

Genomic sequences for E2F-2 may be obtained from any mammalian cell source, whereas mRNA for preparation of cDNA copies may be obtained from cell sources that produce E2F-2. Mammalian cell lines can be used as a convenient source of DNA or RNA.

The E2F-2 coding sequence may be obtained by cDNA cloning of RNA isolated and purified from such cellular sources or by genomic cloning. Either cDNA or genomic libraries may be prepared from the DNA fragments generated using techniques well known in the art, including but not limited to the use of restriction enzymes. The fragments which encode E2F-2 may be identified by screening such libraries with an oligonucleotide or DNA probe that is substantially complementary to any portion of the derived E2F-2 sequences, for instance, the DNA dervied from the highly conserved DNA binding region of E2F-1. Such a technique is illustrated in the Example. To these ends, techniques well known to those skilled in the art for the isolation of DNA, generation of appropriate restriction fragments, construction of clones and libraries, and screening recombinants may be used. For a review of such techniques see, for example, Maniatis et al., 1982, Molecular Cloning: A Laboratory Manual, Cold Spring Harbor Press, New York, Chapters 1–11. Alternatively, oligonucleotides derived from E2F-2 amino acid sequences could be used as degenerate primers in PCR (polymerase chain reactions) to generate cDNA or genomic copies of E2F-2 sequences from a variety of cellular sources. For a review of such PCR techniques, see for example, Gelfand, D. H., 1989, "PCR Technology. Principles and Applications for DNA Amplification," Ed., H. A. Erlich, Stockton Press, New York; and "Current-Protocols in Molecular Biology," Vol. 2, Ch. 15, Eds. Ausubel et al., John Wiley & Sons, 1988.

Alternatively, the coding sequence of the E2F-2 gene could be synthesized in whole or in part, using chemical methods well known in the art. See, for example, Caruthers, et al., 1980, Nuc. Acids Res. Symp. Ser. 7:215–233; Crea and Horn, 1980, Nuc. Acids. 9(10): 2331; Matteucci and Caruthers, 1980, Tetrahedron Letters 21:719; and Chow and Kempe, 1981, Nuc. Acids Res. 9(12) 2807–2817.

Once the cDNA which encodes E2F-2 is obtained through any of the above-noted techniques, the E2F-2 protein of this invention may be prepared in a process comprising the steps of: a) culturing appropriate host cells that have been transformed with and which express a DNA sequence encoding E2F-2; and b) recovering the E2F-2 protein from the culture.

When the E2F-2 protein of this invention is produced by expression in a unicellular host transformed with a DNA sequence encoding the protein, the DNA sequence should be operatively linked to an expression control sequence in an appropriate expression vector and employed in that vector to transform an appropriate unicellular host. Such operative linking of a DNA sequence encoding the E2F-2 protein of this invention to an expression control sequence, of course, includes the provision of a translation start signal in the correct reading frame upstream of that DNA sequence. If the particular DNA sequence to be expressed does not begin with a methionine, the start signal will result in an additional amino acid—methionine—being located at the N-terminus of the product. While such methionyl-containing E2F-2 may be employed directly in the compositions and methods of this invention, it is usually more desirable to remove the methionine before use. Methods are available in the art to remove such N-terminal methionines from polypeptides expressed with them. For example, certain hosts and fermentation conditions permit removal of substantially all of the N-terminal methionine in vivo. Other hosts require in vitro removal of the N-terminal methionine. Such in vivo and in vitro methods are well known in the art.

To facilitate the purification of recombinant E2F-2, additional amino acid sequences can be added in-frame to either the full-length protein or partial sequences of the protein which provide for rapid affinity purification of the resulting fusion protein. For instance, glutathione-S-transferase (GST) binds to glutathione immobilized on a suitable matrix (Smith and Johnson, Gene 67 (1988) 31). The bound protein can be eluted by treating the resin with excess glutathione. The combination of a GST sequence in-frame with an E2F-2 sequence generates a chimeric protein which is readily purified from cell lysates by chromatography on glutathione-S-sepharose. Alternatively, amino acid sequences which bind to a monoclonal antibody can be added inframe at either end of the full-length E2F-2 protein or partial sequences of the protein. For example, immobilized YL1/2 monoclonal antibody binds proteins containing the Glu-Glu-Phe sequence (Stammers et al., FEBS Letters, 283 (1991) 298–302). The bound proteins can be eluted by treating the YL1/2 resin with a solution containing the Asp-Phe dipeptide. A fusion protein containing the Glu-Glu-Phe sequence in frame with amino acid sequences derived from E2F-2 can thus be purified on a suitable support matrix containing immobilized YL1/2 antibody.

A wide variety of host/expression vector combinations may be employed in expressing DNA sequences encoding the E2F-2 of this invention. Useful expression vectors, for example, may consist of segments of chromosomal, non-chromosomal and synthetic DNA sequences, such as various known derivatives of SV40 and known bacterial plasmids, e.g., plasmids from *E. coli*, including col E1, pCR1, pBR322, pMB9, pET-3A and their derivatives, wider host range plasmids, e.g., RP4, phage DNAs, e.g., the numerous derivatives of phage λ, e.g., NM989, and other DNA phages, e.g., M13 and filamentous single-stranded DNA phages, yeast plasmids, such as the 2μ plasmid or derivatives thereof, and vectors derived from combinations of plasmids and phage DNAs, such as plasmids which have been modified to employ phage DNA or other expression control sequences. For bacteria cell expression, we prefer to use plasmid pGEX-2T.

In addition, any of a wide variety of expression control sequences—sequences that control the expression of a DNA sequence when operatively linked to it—may be used in these vectors to express DNA sequences encoding the E2F-2 protein of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. For animal cell expression, a variety of different plasmids and control sequences may be used including, for example, but not limited to, the cytomegalovirus promoter or the adenovirus major late promoter augmented by the SV40 enhancer. Those of skill in the art would recognize a variety of promoters, enhancers, splicing signals, and polyadenylation signals that would be useful for animal cell expression of E2F-2.

A wide variety of unicellular host cells are also useful in expressing DNA sequences encoding the E2F-2 protein of this invention. These hosts may include well known eukaryotic and prokaryotic hosts, such as strains of *E. coli*, Pseudomonas, Bacillus, Streptomyces, Saccharomyces and other fungi, animal cells, such as Chinese hamster ovary ("CHO") and mouse cells in culture, African green monkey cells, such as COS 1, COS 7, BSC 1, BSC 40, and BMT 10, insect cells in culture, human cells in culture and plant cells in culture. For bacteria cell expression, we prefer DH5α (GIBCO BRL) and BL21(DE3) (Novagen) cells.

It should of course be understood that not all vectors and expression control sequences will function equally well to express DNA sequences encoding the E2F-2 protein of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered, as the vector must replicate in it. The vector's copy number, the ability to control that copy number and the expression of any other proteins encoded by the vector, such as antibiotic markers, should also be considered.

In selecting an expression control sequence, a variety of factors should also be considered. These include, for example, the relative strength of the system, its controllability and its compatibility with the DNA sequence encoding the particular E2F-2 of this invention, particularly with respect to potential secondary structures. Unicellular hosts should be selected by consideration of their compatibility with the chosen vector, any potential toxicity of the product coded for upon expression of the DNA sequences of this invention to them, their secretion characteristics, their ability to fold proteins correctly, their fermentation requirements and the ease of purification of the products coded for upon expression of DNA sequences encoding the particular E2F-2 protein of this invention.

The E2F-2 protein produced upon expression of the DNA sequences of this invention may be isolated from fermentation cultures or animal cell cultures and purified using any of a variety of conventional methods, some of which have been previously described. One of skill in the art may select the most appropriate isolation and purification techniques without departing from the scope of this invention. Furthermore, the E2F-2 protein itself could be produced using chemical methods to synthesize the amino acid sequence in whole or in part. For example, peptides can be synthesized by solid phase techniques, cleaved from the resin, and purified by preparative high performance liquid chromatography. (E.g., see, Creighton, 1983, Proteins Structures and Molecular Principles, W. H. Freeman and Co., New York, pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., New York, pp. 34–49).

In order to illustrate the specific embodiments of the invention in greater detail, the following exemplary laboratory preparative work was carded out.

EXAMPLE

Nucleic Acid Reagents

All oligonucleotides were from Midland Certified Reagent Company. Dideoxy sequencing was performed using Sequenase (U.S. Biochemical Corp.) or the Cyclist DNA Sequencing Kit (Stratagene). All cloned DNAs that were generated by polymerase chain reaction (PCR) were sequenced in their entirety to rule out the possibility of polymerase-introduced errors. PCR was performed using Taq polymerase and reagents from Perkin Elmer Cetus.

Identification of the Minimal DNA Binding Domain of E2F-1.

Previous deletion analyses by other groups have shown that amino acids (a.a.) 90–191 or 123–224 retain site-specific DNA binding activity when expressed as GST fusion proteins. Both N- and C-terminal deletions were generated within the E2F-1 (90–191) domain, and the resulting fragments were expressed as GST fusion proteins in *E. coli*. DNA fragments of E2F-1 sequence are amplified by PCR from plasmid pCMV-RBP3 (described by K. Helin et al., *Cell*, 70:337–350 (1992)) using the following primers: E2F-1 (90–191) with e20 and e24; E2F-1 (90–170) with e20 and e25; E2F-1 (90–150) with e20 and e26; E2F-1 (90–130) with e20 and e27; E2F-1 (110–191) with e21 and e24; E2F-1 (120–191) with f120 and e24; E2F-1 (130–191) with e22 and e24; E2F-1 (150–191) with e23 and e24; E2F-1 (110–170) with e21 and e25.

The sequence of the primers is as follows:

| | |
|---|---|
| e20: 5'-CCAGGATCCCGGAGGCTGGACCTGGAAACTG-3'. | (SEQ. ID. NO.: 5) |
| e21: 5'-CCAGGATCCGGCAGAGGCCGCCATCCAGG-3'. | (SEQ. ID. NO.: 6) |
| e22: 5'-CCAGGATCCACCTCACTGAATCTGACCACC-3'. | (SEQ. ID. NO.: 7) |
| e23: 5'-CCAGGATCCGTCGTCGACCTGAACTGGGC-3'. | (SEQ. ID. NO.: 8) |
| e24: 5'-GCGGAATTCTACAGCCACTGGATGTGGTTCTTGG-3'. | (SEQ. ID. NO.: 9) |
| e25: 5'-GCGGAATTCTAGATGTCATAGATGCGCCGCTTC-3'. | (SEQ. ID. NO.: 10) |
| e27: 5'-GCGGAATTCTAGGTCTCATAGCGTGACTTCTC-3'. | (SEQ. ID. NO.: 11) |
| f120: 5'-CCAGGATCCAAATCCCCCGGGGAGAAG-3'. | (SEQ. ID. NO.: 12) |

The amplified fragments were digested with BamHI and EcoRI, cloned into pGEX-2T (Pharmacia) digested with BamHI and EcoRI, and sequenced.

Expression of the GST fusion proteins was induced as previously described by DeFeo-Jones et al. (J. Virol., 67:716–725 (1993)). Specifically, the GST fusion protein constructs for deletion variants of E2F-1 described above were transfected into DH5α cells (GIBCO BRL). Overnight cultures were diluted 1/10 into Luria broth containing 50 µg of ampicillin per ml. Cultures were grown to a $A_{600}$ of 0.6 and isopropyl-β-D-thiogalactopyranoside (IPTG; Sigma, St. Louis, Mo.) was added to a final concentration of 1 mM. After an additional 2 hours, cells were collected by centrifugation and lysates prepared by one round of freezing and thawing, followed by suspension in phosphate-buffered saline (0.2 ml per ml of cells at 1 $A_{600}$ unit) and sonication. Lysates were clarifed by centrifugation, and the relative amounts of GST fusion proteins expressed were determined by immunoblot analysis using a rabbit anti-GST antibody.

Figure 2B:
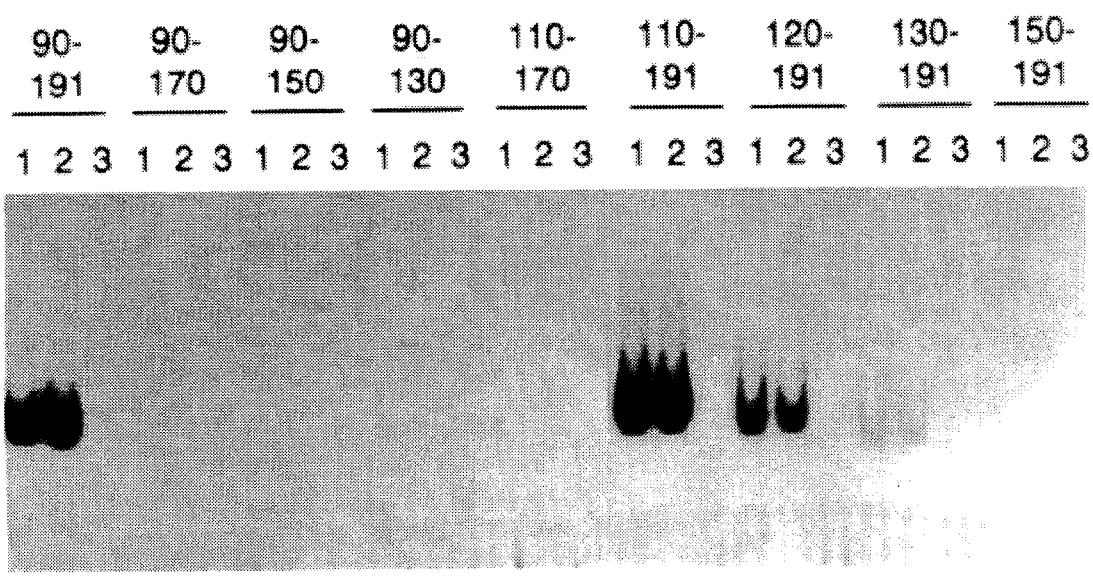

The ability of these fusion proteins to bind specifically to an E2F DNA binding site was determined in a gel shift assay (FIG. 2). The assay and buffer conditions were as previously described by Huber et al. (Proc. Natl. Acad. Sci. U.S.A., 90:3525–3529 (1993)). Crude lysates containing approximately equal amounts of GST-fusion proteins were incubated with $^{32}$P-end-labeled, double stranded DNA probe containing a single pallindromic E2F site (underlined): 5'-TAGTTTTCGATAT-TAAATTTGAGTTTTCGCGCGAAACTAG-3'. (SEQ.ID.NO.: 13) Cold competitor DNA contained either a wild-type E2F site or a mutated site (TTTCGATCCAAA) (SEQ.ID.NO.: 14). Amino acids 90–109 appeared to be dispensible for DNA binding, since GST-E2F-1 (110–191) exhibits wild-type activity. However, any additional deletions resulted in proteins with reduced DNA binding activity. GST-E2F-1 (120–191) showed reduced activity, while deletion of amino acids 171–191 from the C-terminus of the DNA-binding domain resulted in a complete loss of DNA binding activity. Based on these results, amino acids 110–191 appear to encode the fully active DNA binding domain of E2F-1. Significant structural features of this region include a cluster of basic residues (a.a. 109–127) followed by overlapping helix-loop-helix (a.a. 128–181) and hydrophobic repeat (a.a. 153–174) domains.

Isolation of E2F-2 cDNA by Library Screening

Figure 3A:
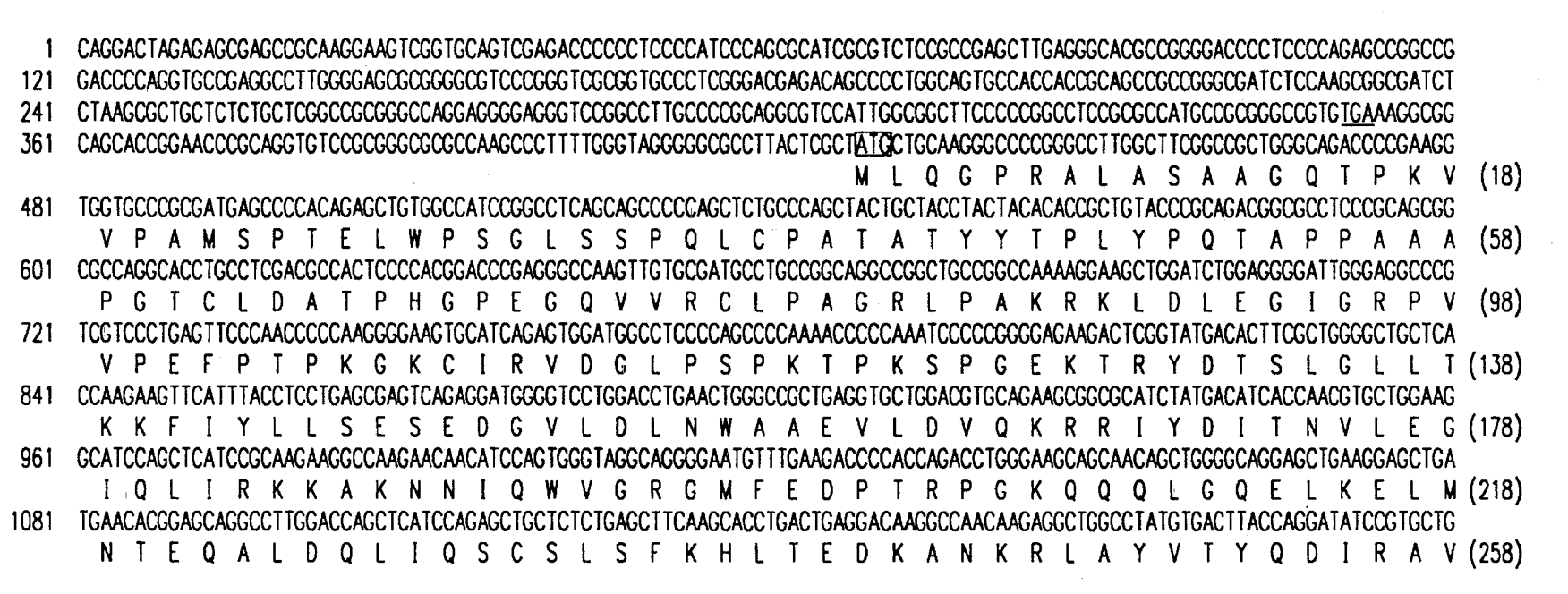

Nitrocellulose plaque lifts from a human HeLa S3 cDNA λgt11 library (Clontech) were hybridized under low stringency conditions with a $^{32}$P-labeled DNA fragment of E2F-1 corresponding to amino acids 110–191. Hybridization was performed in 30% formamide, 5×SSC, 5×Denhardt's, 0.1% SDS, 100 µg/ml salmon sperm DNA at 42° C. for 16 hr or in the same buffer using 25% formamide at 37° C. Filters were washed in 2×SSC, 0.1% SDS at 37° C. twice for 30 min followed by 1×SSC, 0.1% SDS at 37° C. once for 1 hr. Positive clones were identified by autoradiography and were subjected to two further rounds of plaque purification and hybridization. The cDNA inserts from 21 positive clones were partially sequenced, and two clones (#9 and #10) that were clearly distinct from E2F-1 were further characterized. Phage DNA was prepared from the plaque-purified phage stocks of each, and the EcoRI cDNA inserts were subcloned from the phage DNA into pGEX-2T to generate pGEX-9 and pGEX-10. An E. coli cell culture transformed with pGEX-9 has been deposited with the ATCC and has been assigned the number ATCC 69426. Both strands of each cDNA were sequenced and shown to contain overlapping regions of the same gene. The DNA sequence is shown in FIG. 3. (SEQ.ID.NO.: 3) Clone 9 contained a 1766 base pair cDNA (nucleotides 1–1766 of FIG. 3). Clone 10 contained a 1963 base pair cDNA (nucleotides 685–2647 of FIG. 3). The largest open reading frame contained within these overlapping cDNA fragments is 1311 nucleotides long (437 amino acids) (SEQ.ID.NO.: 2) with in frame stop codons both 5' (underlined) and 3' (boxed) to the open reading frame (FIG. 3) and is completely contained in clone 9. The protein encoded by this open reading frame was designated E2F-2 (predicted molecular weight=47.5 kDa).

DNA and amino acid homologies were determined by the "Gap" subroutine of GCG (v. 7.2; Genetics Computer Group, Inc., Madison Wis.). When compared with sequences in the GENBANK data base, E2F-2 showed no significant homology to any known genes other than E2F-1. An amino acid alignment between E2F-2 and E2F-1 is shown in FIG. 4 (overall amino acid identity=46%). (E2F-2 amino acid: SEQ.ID.NO.: 2; E2F-1 amino acid: SEQ.ID.NO.: 4) As expected, the region corresponding to the DNA binding domain of E2F-1 (amino acids 110–191) is highly conserved in E2F-2 (72% amino acid identity). The high degree of conservation in this region includes several basic amino acids (denoted with a "#" in FIG. 4) and hydrophobic residues (denoted with a "*" in FIG. 4) that comprise the amphipathic helices (boxed) of a potential helix-loop-helix structure. Both of the zipper-like structures identified in E2F-1 are conserved in E2F-2 (hydrophobic residues denoted with a "+" and a "‡" respectively in FIG. 4). Thus the entire basic-helix-loop-helix-zipper region predicted for E2F-1 is conserved in E2F-2. Finally, the pRb binding domain of E2F-1 (amino acids 409–426) is also highly conserved (72% identity) in E2F-2 (amino acids 410–427). Homology between E2F-2 and the recently isolated E2F-like DP-1 protein is limited and is similar to that reported between DP-1 and E2F-1.

Plasmid Constructions

The pT5T expression system described by Eisenberg et al. (Nature, 343:341–346 (1990)) was used to express full length E2F-2 (amino acids 1–437) from its natural start codon in E. coli strain BL21 (DE3) (Novagen). PCR was used to amplify the E2F-2 coding region from pGEX-9. The 5' primer used (5'-CCAAGGATCCATTGGAGGATGATTAA<u>ATG</u>CTGCAAGGGCCCC-3')  (SEQ. ID. NO.: 15)

signals upstream of the initiating methionine (underlined) as prescribed for use in the pT5T vector. The 3' primer used (5'-GAGAGCAAGCTTAGAACTCCTCATTAATCAACAGGTCCCCAAGG-3')  (SEQ. ID. NO.: 16)

natural C-terminus of the protein for antibody recognition by the YL1/2 anti-tubulin antibody and also included a HindIII site. The DNA was cloned as a BamHI-HindIII fragment into pT5T digested with BamHi and HindIII to generate pE2F-2-PCR. A large internal fragment of the PCR-generated sequence ( 1185 bp partial ApaI-BclI fragment) was then replaced with the corresponding DNA fragment from pGEX-9 to reduce the possibility of errors. The PCR-generated sequences 5' and 3' to the exchanged fragment were sequenced in their entirety. The final product was designated pE2F-2.

A pT5T plasmid expressing full length E2F-1 (amino acids 1–437) with the C-terminal Glu-Glu-Phe added was constructed by the same approach. The sequence of the 5' primer was 5'-CCAGAGGATCCATTGGAGGATGATTAA<u>ATG</u>GCCTTGGCCGGGGCCCC-3'  (SEQ. ID. NO.: 17)

and the 3' primer was

5'-GAGAGCAAGCTTCTAGAACTCCTCGAAATCCAGGGGGGTGAGGTCC-3'.  (SEQ. ID. NO.: 18)

A 1230 bp ApaI-XhoI fragment from the PCR clone was replaced with the corresponding E2F-1 fragment from pBSK-BP3-B to generate pE2F-1.

To construct a vector which would express full length E2F-2 (amino acids 1–437) as a glutathione S-transferase (GST) fusion, pGEX-9 was digested to completion with BamHI and EclXI to remove the 5' untranslated region and the sequence encoding the first ten amino acids of the open reading frame. A synthetic oligonucleotide BamHI-EclXI cassette was inserted which restored the coding sequence of the first ten amino acids and fused them in frame with the upstream GST sequences. The sequence of the complementary oligonucleotides comprising the cassette were:

5'-GATCCATGCTGCAAGGGCCCCGGGCCTTGGCTTC-3'  (SEQ. ID. NO.: 19)
and
5'-GGCCGAAGCCAAGGCCCGGGGCCCTTGCAGCATG-3'.  (SEQ. ID. NO.: 20)

The resulting plasmid was designated pGEX-E2F-2.

GST fusion protein constructs for deletion variants of E2F-2 were prepared exactly as described above for E2F-1 using pGEX-9 as template and the following primers: E2F-2 (87–244) with f-90 and 9-21; E2F-2 (87–193) with f-90 and f-191; E2F-2 (112–193) with f-110 and f-191; E2F-2 (122–193) with f-120 and f-191; E2F-2 (132–193) with f-130 and f-191; E2F-2 (152–193) with f-150 and f-191; E2F-2 (410–427) with 9R and 9B. The sequence of the primers was as follows:

f-90: 5'-CCAGGATCCAAAAGGAAGCTGGATCTGGAGG-3'. (SEQ. ID. NO.: 21)
f-110: 5'-CCAGGATCCGTGGATGGCCTCCCCAGC-3'. (SEQ. ID. NO.: 22)
f-120: 5'-CCAGGATCCAAATCCCCCGGGGAGAAG-3'. (SEQ. ID. NO.: 23)
f-130: 5'-CCAGGATCCACTTCGCTGGGGCTGCTCAC-3'. (SEQ. ID. NO.: 24)
f-150: 5'-CCAGGATCCGTCCTGGACCTGAACTGGG-3'. (SEQ. ID. NO.: 25)
f-191: 5'-GCGGAATTCTATACCCACTGGATGTTGTTCTTGGC-3'. (SEQ. ID. NO.: 26)
9-21: 5'-GCGGAATTCAGTTGGCCTTGTCCTCAGTC-3'. (SEQ. ID. NO.: 27)
9R: 5'-GGACGGATCCGACGACTACCTGTGGGGCTTG-3'. (SEQ. ID. NO.: 28)
9B: 5'-CCTCGAATTCAGTCGAAGAGATCGCTGATGCC-3'. (SEQ. ID. NO.: 29)

Northern Blot Analyses

A human multiple tissue Northern blot (Clontech) was hybridized with a $^{32}$P random-labeled DNA fragment corresponding to the E2F-2 clone 9 cDNA using QuikHyb Hybridization Solution (Stratagene) and washed as recommended by the manufacturer. Tumor cell lines were obtained from the American Type Culture Collection (Rockville, Md.) and grown in the recommended medium at 37° C. in a 6% $CO_2$-containing atmosphere. Poly (A$^+$) RNA was isolated using the Fast Track mRNA Isolation Kit (Invitrogen) according to the manufacturer's procedure. The poly (A$^+$) RNA (2 μg) was denatured and separated on a 1% agarose formaldehyde-containing gel as described in Molecular Cloning: A Laboratory Manual. The RNA was then transferred to a Zeta-Probe membrane (BioRad) and hybridized with an E2F-2 probe as above. Blots were hybridized a second time with a $^{32}$P random-labeled 2 kb fragment of human actin DNA as a control probe.

Figure 5B:
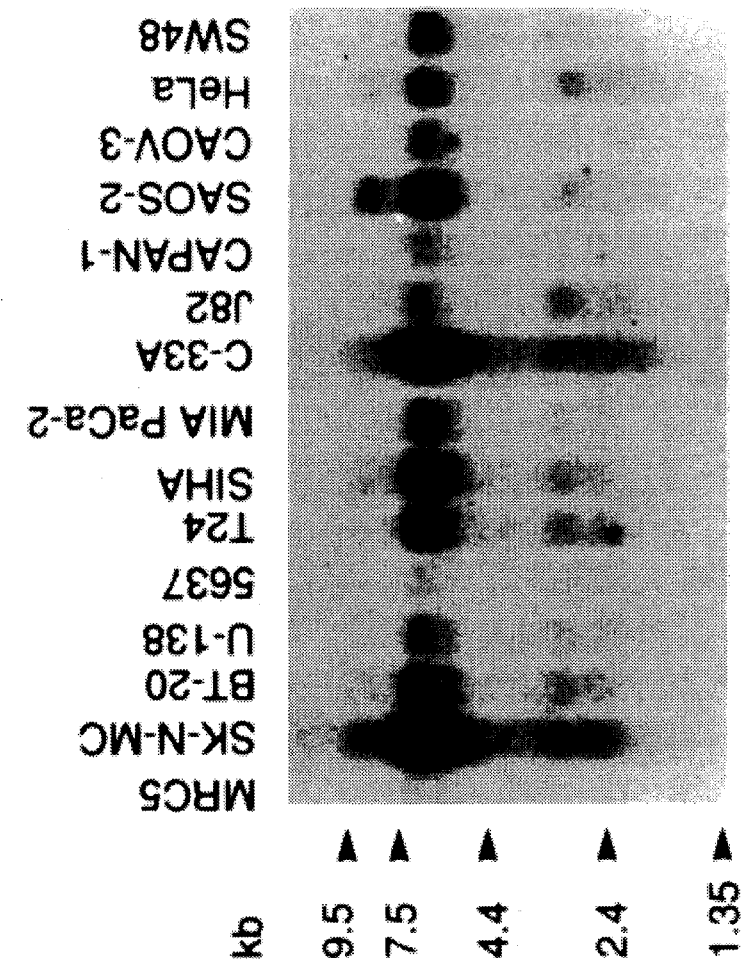
FIG. 5. "Northern" blot analysis of E2F-2 mRNA. Poly-($A^+$) selected RNA extracted from normal human tissue (Panel A) or various cell lines (Panel B) was probed with E2F-2 clone 9 cDNA (upper sets). As a control, the same blots were probed with actin cDNA (lower sets).
Figure 5A:
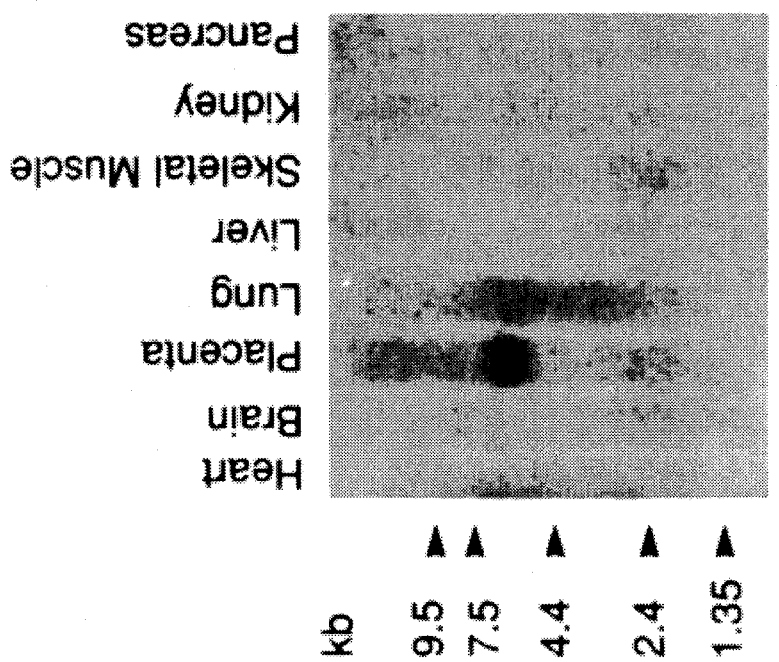

As shown in FIG. 5A, among eight tissues examined, only placenta showed a readily detectable level of E2F-2 mRNA. The size of the message (approximately 6 kb) cannot be accurately determined due to the poor resolution of larger RNAs. We also examined poly (A$^+$) RNA from 32 cell lines corresponding to 13 different tumor types, of which a representative set is shown in FIG. 5B. The approximately 6 kb E2F-2 mRNA was present in all cell lines, although at varying levels. Other species of approximately 2.5, 3.0 and 8 kb were also detected in some cell lines. The mRNA represented by the band at approximately 3.0 kb is likely to be the homologous E2F-1 message, since a band in precisely the same position appears when the blot is probed with E2F-1 cDNA, and it corresponds to the size expected for E2F-1 based on previous reports by Helin et al. (Cell, 70:337–350 (1992)) and Kaelin et al. (Cell, 70:351–364 (1992)). The MRC5 primary lung fibroblasts exhibited an extremely low level of E2F-2 mRNA. Apart from the general observation that the cancer cell lines appear to display higher levels of E2F-2 mRNA than primary cell cultures no obvious correlation between tumor origin and E2F-2 message levels was observed.

Expression and Gel Mobility Shift Assays of GST-E2F-2 Fusion Proteins

Figures 6A, 6B, 6C:
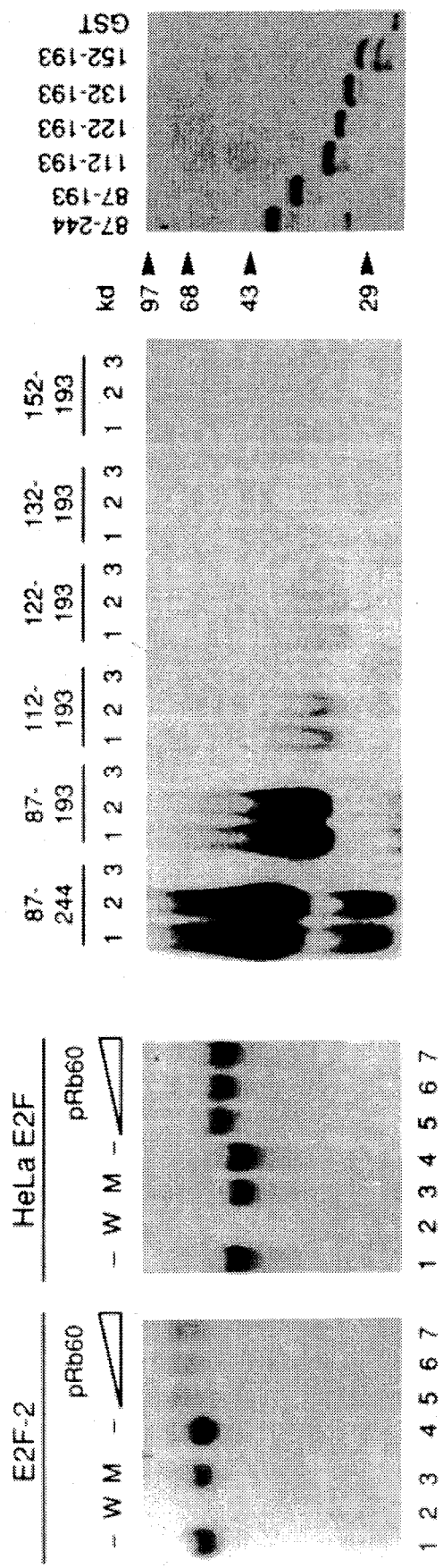
FIG. 6. Gel shift analysis of E2F-2. Panel A—Full length tubulin-tagged E2F-2 (left panel) and affinity-purified HeLa E2F (right panel) were analyzed in the gel-shift assay. Lanes 1, 4–7—no competitor; lane 2—includes excess wild-type competitor DNA; lane 3—includes excess mutant competitor DNA; lanes 5–7—includes increasing concentrations of recombinant pRb60. Panel B—GST-E2F-2 fusion proteins containing the indicated E2F-2 amino acids were assayed as soluble *E. coli* lysates in the gel-shift assay. Lane 1—no competitor; lane 2—includes excess mutant competitor DNA; lane 3—contains excess wild-type competitor DNA. Panel C—"Western" blot analysis of the lysates tested in Panel B using an anti-GST polyclonal antibody.

Expression of the GST fusion proteins was induced as described above for the GST-E2F-1 fusion proteins. The results of the gel shift assay are shown in FIG. 6B for E2F-2. These results demonstrate that E2F-2 binds specifically to an E2F DNA binding sequence.

The full length E2F-2 protein was similarly expressed as a GST fusion using the pGEX-E2F-2 plasmid described above.

Purification and Gel Mobility Shift Assays of Recombinant Proteins and HeLa E2F Full length E2F-2 protein with the C-terminal tubulin tripeptide epitope was expressed in transformed BL21(DE3) cells essentially as described for the expression in DH5α cells (however, induction was at room temperature for 2 hours) and affinity purified essentially as described by Stammers et al. (FEBS Letters, 283:298–302 (1991)).

Specifically, YL1/2 rat ascites fluid was obtained from Serotec (Oxford, UK). IgGs were purified from this fluid by ammonium sulfate fractionation and ion exchange on DEAE-cellulose (DE52, Whatman) and coupled to CNBr-activated Sepharose (1 g/10 mg of IgG) as per manufacturer's instructions (Pharmacia). Columns of YL1/2-Sepharose were equilibrated in 50 mM NaCl, 50 mM Tris-HCl, pH 7.5. After placing the crude extract on the column, the column was eluted with running buffer containing 5 mM Asp-Phe (Sigma).

The affinity purified protein was electroeluted from an SDS polyacrylamide gel as previously described by Huber et al. (Proc. Natl. Acad. Sci. U.S.A., 90:3525–3529 (1993)). Specifically, the gel slices containing E2F-2 were electroeluted into 20 mM ammonium bicarbonate/0.01% SDS with an Amicon Centrilutor, and concentrated 10:1 in Centricon 30 concentrators.

The conditions for the gel shift assay, the affinity purification of HeLa E2F, and the purification of recombinant pRb60 have been previously described (see Huber et al., Proc. Natl. Acad. Sci. U.S.A., 90:3525–3529 (1993) and Edwards et al., J.Biol. Chem. 267:7971–7974 (1992)). Denatured salmon sperm DNA was included in the assay at 2 μg/ml. The E2F-2 protein was compared to purified HeLa cell E2F in a gel mobility shift assay (FIG. 6, part A). As seen with HeLa cell E2F, E2F-2 protein bound to a DNA probe containing an E2F consensus sequence, and the binding was specific since it was competed with excess unlabeled wild-type, but not mutant, E2F oligonucleotide. The mobility of the E2F-2 DNA complex was reduced by the addition of purified pRb60 protein, as was also the case for HeLa E2F (FIG. 6, part A). Thus recombinant E2F-2 exhibits two important properties of cellular E2F, sequence-specific DNA binding and association with pRb.

In vitro Binding Assays

Bacterial lysates containing GST fusion proteins were made as described above. The relative amounts of the GST fusion proteins in the lysates (as determined by immunoblot analysis using anti-GST antibody) were normalized using lysate without GST fusion protein.

For pRb60 binding assays, 50 µl of normalized lysates were incubated with or without 0.6 µg purified pRb60 in a final volume of 100 µl phosphate-buffered saline-0.1% NP40 for 1.5 hr at 4° C. Where indicated, partially purified GST-E1A was also included in the binding reaction as a competitor. The pRb60 and any associated proteins were then recovered using monoclonal anti-pRb antibody XZ55 (prepared as descibed in G. Hu et al., *Mol. Cell. Biol.*, 11:5792–5799 (1991)), followed by rabbit anti-mouse IgG (Cappel) and Protein A-Sepharose beads (Pharmacia). The beads were washed three times in cold phosphate-buffered saline, and bound proteins were eluted by boiling in SDS-gel loading buffer. Proteins were resolved on a 12% SDS-polyacrylamide gel (Novex), and GST fusion proteins were detected by immunoblot analysis using anti-GST antibody.

Figures 7A, 7B:
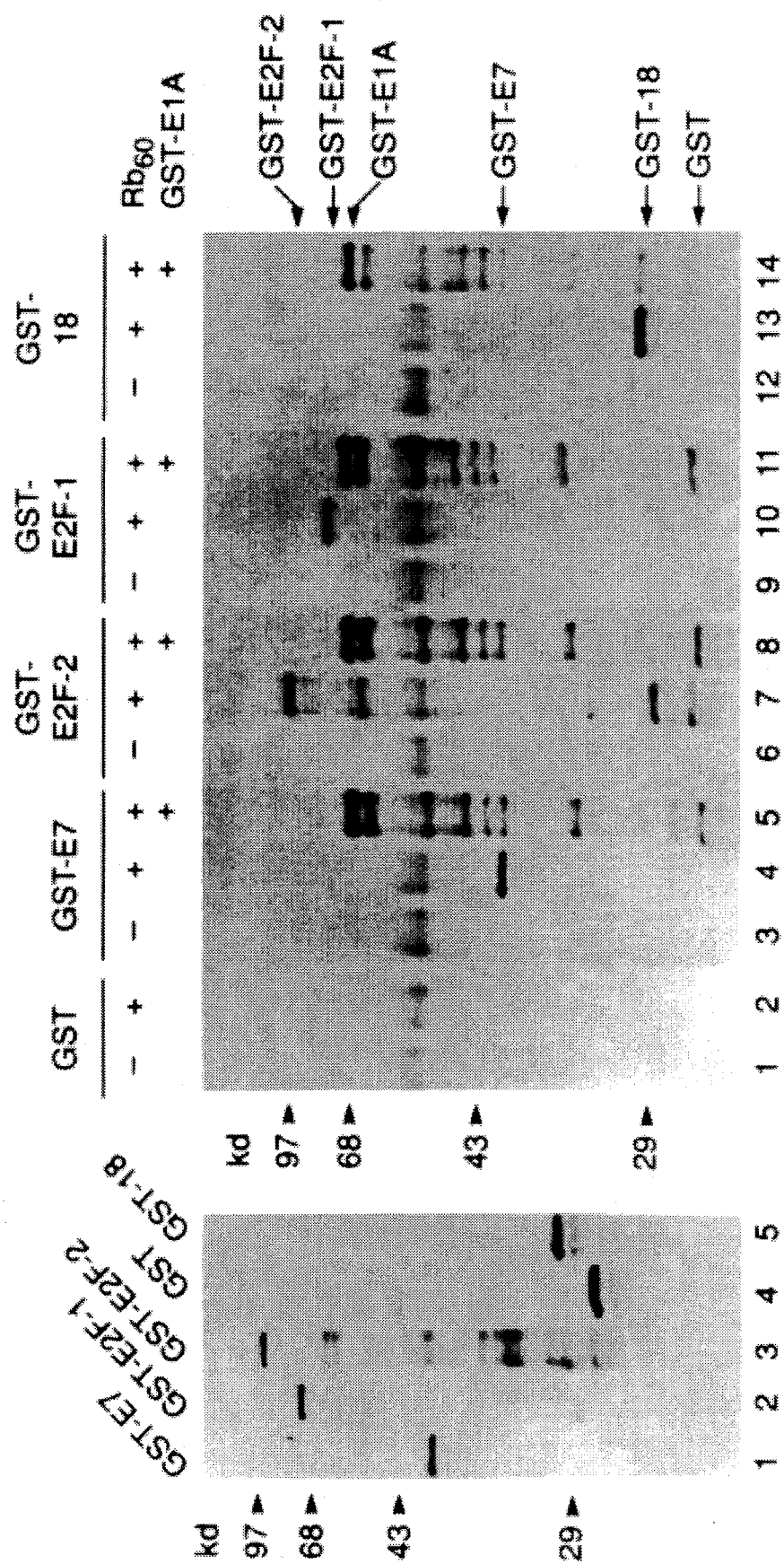
FIG. 7. Binding of E2F-2 protein to pRb60. Soluble *E. coli* lysates containing the indicated GST fusion protein were incubated in the presence (lanes 2, 4, 5, 7, 8, 10, 11, 13, 14) or absence (lanes 1, 3, 6, 9, 12) of 100 nM recombinant pRb60 and immunoprecipitated with an anti-pRb monoclonal antibody. The immunoprecipitate was analyzed by SDS-PAGE and "Western" blotting with an anti-GST polyclonal antibody. The positions of each GST fusion protein in the "Western" blot is indicated along the right side. Affinity-purified GST-E1A was used as a competitor for pRb binding in the third lane of each set (lanes 5, 8, 11, 14).

The GST fusion proteins tested are shown in FIG. 7. GST-E7 and GST-E2F-1 (amino acids 89–437) which have both been previously shown to bind to pRb60, were included as positive controls. GST-E2F-2 is a fusion protein containing the complete coding sequence of E2F-2, and GST-18 is a fusion protein containing the 18 amino acid region of E2F-2 (410–427) which is homologous to the 18 amino acid pRb-binding region of E2F-1 (409–426). As shown in FIG. 7, GST alone did not bind to pRb60. GST-E7, GST-E2F-2, GST-E2F-1 and GST-18 were immunoprecipitated by anti-pRb antibodies in the presence (lanes 2, 4, 5, 7, 8, 10, 11, 13 and 14) but not in the absence (lanes 1, 3, 6, 9, and 12) of pRb60. Thus, the 18 amino acid region at the C-terminus of E2F-2 is sufficient for specific association with the pocket region of pRb. In addition, the binding of all of the GST-fusion proteins to pRb60 was inhibited by the addition of GST-E1A (lanes 5, 8, 11, and 14).

Silver Staining

Silver staining of SDS-PAGE gels was performed using the Quick-silver kit from Amersham.

E2F-2 DNA Binding Activity is Enhanced by Heterodimerization

To determine whether the biochemical behavior of E2F-2 is consistent with the complementation model of E2F and is therefore part of the E2F protein family, and to assess whether E2F-2 acts as the normal binding partner of E2F-1, mixing experiments between E2F-2, gel-purified components of HeLa cell E2F, and recombinant E2F-1 were performed. Tubulin-tagged E2F-1 and E2F-2 were used at 5 and 2 µg/ml, respectively and the individually purified HeLa E2F components were separated and gel eluted as described by Huber et al., *Proc. Natl. Acad. Sci USA*, 90:3525–3529 (1993).

E2F DNA binding activity was monitored in the gel-shift assay (FIG. 8A). Recombinant purified full-length E2F-1 and E2F-2 and HeLa cell E2F components were titrated to yield no detectable signal under these assay conditions. Upon denaturing and refolding E2F-2 in the presence of the lower molecular-weight component of HeLa E2F (Band 1), a very strong gel-shift band was observed (lane 3) which co-migrated with authentic E2F (lane 1). No band was observed upon co-refolding of E2F-2 with the higher molecular weight component of HeLa E2F (Band 5) (lane 4). These results were identical to those obtained using recombinant E2F-1 in place of E2F-2 (lanes 5–7), which suggests that these two proteins belong to the same complementation group. In support of this hypothesis, co-refolding of E2F-1 and E2F-2 yielded no detectable gel-shift band (lane 8). As previously reported, the proteins contained in band 1 or band 5 did not generate any signal when tested individually under these conditions, but a strong band was observed upon mixing these proteins (lanes 9–11). These results are consistent with the previously proposed heterodimerization model of E2F, with E2F-1 and E2F-2 belonging to the same complementation group as the higher molecular-weight component of HeLa cell E2F (band 5).

Additional data in support of this model is provided by analysis of HeLa E2F by a "Western" blot with anti-E2F-2 antibodies. Rabbit polyclonal antisera generated against a non-conserved region of E2F-2 (a.a. 196–210, synthesized as a MAP fusion according to the procedure described by Posnett et al. *J. Biol. Chem.*, 263:1719–1725(1988)) was raised in rabbits and affinity purified by Protein A Sepharose chromatography. This antibody (2.5 µg/ml) was tested for cross-reactivity against HeLa E2F and purified E2F-1 (FIG. 8B and C). As anticipated, this antisera detects E2F-2, but not E2F-1 (FIG. 8C, lanes 2 and 3). In addition, the anti-E2F-2 antisera detects bands 4 and 5 of HeLa E2F (FIG. 8C, lane 1), as judged by overlaying the Western blot autoradiogram (FIG. 8C) on the silver stained gel of the same samples (FIG. 8B). E2F-2 is therefore both functionally and immunologically related to the higher molecular-weight components of authentic HeLa E2F.

What is claimed is:

1. A protein comprising the polypeptide shown in SEQ. I.D. NO.: 2.

2. The protein according to claim 1, wherein the protein is the E2F-2 protein shown in SEQ. ID. NO.: 2.

\* \* \* \* \*

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
      ( A ) LENGTH: 1314 base pairs
      ( B ) TYPE: nucleic acid
      ( C ) STRANDEDNESS: single -continued ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

| ATGCTGCAAG | GGCCCCGGGC | CTTGGCTTCG | GCCGCTGGGC | AGACCCCGAA | GGTGGTGCCC | 60 |
| GCGATGAGCC | CCACAGAGCT | GTGGCCATCC | GGCCTCAGCA | GCCCCAGCT | CTGCCCAGCT | 120 |
| ACTGCTACCT | ACTACACACC | GCTGTACCCG | CAGACGGCGC | CTCCCGCAGC | GGCGCCAGGC | 180 |
| ACCTGCCTCG | ACGCCACTCC | CCACGGACCC | GAGGGCAAG | TTGTGCGATG | CCTGCCGGCA | 240 |
| GGCCGGCTGC | CGGCCAAAAG | GAAGCTGGAT | CTGGAGGGGA | TTGGGAGGCC | CGTCGTCCCT | 300 |
| GAGTTCCCAA | CCCCCAAGGG | GAAGTGCATC | AGAGTGGATG | CCTCCCCAG | CCCCAAAACC | 360 |
| CCCAAATCCC | CCGGGGAGAA | GACTCGGTAT | GACACTTCGC | TGGGGCTGCT | CACCAAGAAG | 420 |
| TTCATTTACC | TCCTGAGCGA | GTCAGAGGAT | GGGGTCCTGG | ACCTGAACTG | GGCCGCTGAG | 480 |
| GTGCTGGACG | TGCAGAAGCG | GCGCATCTAT | GACATCACCA | ACGTGCTGGA | AGGCATCCAG | 540 |
| CTCATCCGCA | AGAAGGCCAA | GAACAACATC | CAGTGGGTAG | GCAGGGGAAT | GTTTGAAGAC | 600 |
| CCCACCAGAC | CTGGGAAGCA | GCAACAGCTG | GGCAGGAGC | TGAAGGAGCT | GATGAACACG | 660 |
| GAGCAGGCCT | TGGACCAGCT | CATCCAGAGC | TGCTCTCTGA | GCTTCAAGCA | CCTGACTGAG | 720 |
| GACAAGGCCA | ACAAGAGGCT | GGCCTATGTG | ACTTACCAGG | ATATCCGTGC | TGTTGGCAAC | 780 |
| TTTAAGGAGC | AGACAGTGAT | TGCCGTCAAG | GCCCCTCCGC | AGACGAGACT | GGAAGTGCCC | 840 |
| GACAGGACTG | AGGACAACCT | GCAGATATAT | CTCAAGAGCA | CCCAAGGGCC | CATCGAAGTC | 900 |
| TACCTGTGCC | AGAGGAGGT | GCAGGAGCCG | GACAGTCCTT | CCGAGGAGCC | TCTCCCCTCT | 960 |
| ACCTCCACCC | TCTGCCCCAG | CCCTGACTCT | GCCCAGCCCA | GCAGCAGCAC | CGACCCTAGC | 1020 |
| ATCATGGAGC | CCACAGCATC | CTCAGTGCCA | GCACCAGCGC | CAACCCCCCA | GCAGGCCCCA | 1080 |
| CCGCCTCCAT | CCCTGGTCCC | CTTGGAGGCT | ACTGACAGCC | TGCTGGAGCT | GCCGCACCCA | 1140 |
| CTCCTGCAGC | AGACTGAGGA | CCAGTTCCTG | TCCCCGACCC | TGGCGTGCAG | CTCCCCTCTG | 1200 |
| ATCAGCTTCT | CCCCATCCTT | GGACCAGGAC | GACTACCTGT | GGGGCTTGGA | GGCGGGTGAG | 1260 |
| GGCATCAGCG | ATCTCTTCGA | CTCCTACGAC | CTTGGGGACC | TGTTGATTAA | TTGA | 1314 |

( 2 ) INFORMATION FOR SEQ ID NO:2:

( i ) SEQUENCE CHARACTERISTICS:
( A ) LENGTH: 437 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

```
Met Leu Gln Gly Pro Arg Ala Leu Ala Ser Ala Ala Gly Gln Thr Pro
 1               5                  10                  15

Lys Val Val Pro Ala Met Ser Pro Thr Glu Leu Trp Pro Ser Gly Leu
            20                  25                  30

Ser Ser Pro Gln Leu Cys Pro Ala Thr Ala Thr Tyr Tyr Thr Pro Leu
        35                  40                  45

Tyr Pro Gln Thr Ala Pro Pro Ala Ala Ala Pro Gly Thr Cys Leu Asp
    50                  55                  60
```

```
Ala  Thr  Pro  His  Gly  Pro  Glu  Gly  Gln  Val  Val  Arg  Cys  Leu  Pro  Ala
65                  70                       75                            80

Gly  Arg  Leu  Pro  Ala  Lys  Arg  Lys  Leu  Asp  Leu  Glu  Gly  Ile  Gly  Arg
                    85                       90                  95

Pro  Val  Val  Pro  Glu  Phe  Pro  Thr  Pro  Lys  Gly  Lys  Cys  Ile  Arg  Val
               100                      105                       110

Asp  Gly  Leu  Pro  Ser  Pro  Lys  Thr  Pro  Lys  Ser  Pro  Gly  Glu  Lys  Thr
               115                      120                       125

Arg  Tyr  Asp  Thr  Ser  Leu  Gly  Leu  Leu  Thr  Lys  Lys  Phe  Ile  Tyr  Leu
          130                      135                 140

Leu  Ser  Glu  Ser  Glu  Asp  Gly  Val  Leu  Asp  Leu  Asn  Trp  Ala  Ala  Glu
145                      150                      155                       160

Val  Leu  Asp  Val  Gln  Lys  Arg  Arg  Ile  Tyr  Asp  Ile  Thr  Asn  Val  Leu
                    165                      170                       175

Glu  Gly  Ile  Gln  Leu  Ile  Arg  Lys  Lys  Ala  Lys  Asn  Asn  Ile  Gln  Trp
               180                      185                       190

Val  Gly  Arg  Gly  Met  Phe  Glu  Asp  Pro  Thr  Arg  Pro  Gly  Lys  Gln  Gln
          195                      200                       205

Gln  Leu  Gly  Gln  Glu  Leu  Lys  Glu  Leu  Met  Asn  Thr  Glu  Gln  Ala  Leu
210                           215                      220

Asp  Gln  Leu  Ile  Gln  Ser  Cys  Ser  Leu  Ser  Phe  Lys  His  Leu  Thr  Glu
225                      230                      235                       240

Asp  Lys  Ala  Asn  Lys  Arg  Leu  Ala  Tyr  Val  Thr  Tyr  Gln  Asp  Ile  Arg
                    245                      250                       255

Ala  Val  Gly  Asn  Phe  Lys  Glu  Gln  Thr  Val  Ile  Ala  Val  Lys  Ala  Pro
               260                      265                       270

Pro  Gln  Thr  Arg  Leu  Glu  Val  Pro  Asp  Arg  Thr  Glu  Asp  Asn  Leu  Gln
          275                      280                       285

Ile  Tyr  Leu  Lys  Ser  Thr  Gln  Gly  Pro  Ile  Glu  Val  Tyr  Leu  Cys  Pro
290                           295                      300

Glu  Glu  Val  Gln  Glu  Pro  Asp  Ser  Pro  Ser  Glu  Glu  Pro  Leu  Pro  Ser
305                      310                      315                       320

Thr  Ser  Thr  Leu  Cys  Pro  Ser  Pro  Asp  Ser  Ala  Gln  Pro  Ser  Ser  Ser
                    325                      330                       335

Thr  Asp  Pro  Ser  Ile  Met  Glu  Pro  Thr  Ala  Ser  Ser  Val  Pro  Ala  Pro
               340                      345                       350

Ala  Pro  Thr  Pro  Gln  Gln  Ala  Pro  Pro  Pro  Ser  Leu  Val  Pro  Leu
          355                      360                       365

Glu  Ala  Thr  Asp  Ser  Leu  Leu  Glu  Leu  Pro  His  Pro  Leu  Leu  Gln  Gln
370                      375                      380

Thr  Glu  Asp  Gln  Phe  Leu  Ser  Pro  Thr  Leu  Ala  Cys  Ser  Ser  Pro  Leu
385                      390                      395                       400

Ile  Ser  Phe  Ser  Pro  Ser  Leu  Asp  Gln  Asp  Asp  Tyr  Leu  Trp  Gly  Leu
               405                      410                       415

Glu  Ala  Gly  Glu  Gly  Ile  Ser  Asp  Leu  Phe  Asp  Ser  Tyr  Asp  Leu  Gly
               420                      425                       430

Asp  Leu  Leu  Ile  Asn
          435
```

( 2 ) INFORMATION FOR SEQ ID NO:3:

( i ) SEQUENCE CHARACTERISTICS:
        ( A ) LENGTH: 2647 base pairs
        ( B ) TYPE: nucleic acid
        ( C ) STRANDEDNESS: single -continued ( D ) TOPOLOGY: linear ( i i ) MOLECULE TYPE: cDNA ( x i ) SEQUENCE DESCRIPTION: SEQ ID NO:3:

| | | | | | | |
|---|---|---|---|---|---|---|
| CAGGACTAGA | GAGCGAGCCG | CAAGGAAGTC | GGTGCAGTCG | AGACCCCCT | CCCCATCCCA | 60 |
| GCGCATCGCG | TCTCCGCCGA | GCTTGAGGGC | ACGCCGGGGA | CCCCTCCCCA | GAGCCGGCCG | 120 |
| GACCCCAGGT | GCCGAGGCCT | TGGGGAGCGC | GGGGCGTCCC | GGGTCGCGGT | GCCCTCGGGA | 180 |
| CGAGACAGCC | CCTGGCAGTG | CCACCACCGC | AGCCGCCGGG | CGATCTCCAA | GCGGCGATCT | 240 |
| CTAAGCGCTG | CTCTCTGCTC | GGCCGCGGGC | CAGGAGGGGA | GGGTCCGGCC | TTGCCCCGCA | 300 |
| GGCGTCCATT | GGCGGCTTCC | CCCGGCCTCC | GCGCCATGCC | GCGGGCCGTG | TGAAAGGCGG | 360 |
| CAGCACCGGA | ACCCGCAGGT | GTCCGCGGGC | GCGCCAAGCC | CTTTTGGGTA | GGGGGCGCCT | 420 |
| TACTCGCTAT | GCTGCAAGGG | CCCCGGGCCT | TGGCTTCGGC | CGCTGGGCAG | ACCCCGAAGG | 480 |
| TGGTGCCCGC | GATGAGCCCC | ACAGAGCTGT | GGCCATCCGG | CCTCAGCAGC | CCCCAGCTCT | 540 |
| GCCCAGCTAC | TGCTACCTAC | TACACACCGC | TGTACCCGCA | GACGGCGCCT | CCCGCAGCGG | 600 |
| CGCCAGGCAC | CTGCCTCGAC | GCCACTCCCC | ACGGACCCGA | GGGCCAAGTT | GTGCGATGCC | 660 |
| TGCCGGCAGG | CCGGCTGCCG | GCCAAAAGGA | AGCTGGATCT | GGAGGGGATT | GGGAGGCCCG | 720 |
| TCGTCCCTGA | GTTCCCAACC | CCCAAGGGGA | AGTGCATCAG | AGTGGATGGC | CTCCCCAGCC | 780 |
| CCAAAACCCC | CAAATCCCCC | GGGGAGAAGA | CTCGGTATGA | CACTTCGCTG | GGGCTGCTCA | 840 |
| CCAAGAAGTT | CATTTACCTC | CTGAGCGAGT | CAGAGGATGG | GGTCCTGGAC | CTGAACTGGG | 900 |
| CCGCTGAGGT | GCTGGACGTG | CAGAAGCGGC | GCATCTATGA | CATCACCAAC | GTGCTGGAAG | 960 |
| GCATCCAGCT | CATCCGCAAG | AAGGCCAAGA | ACAACATCCA | GTGGGTAGGC | AGGGGAATGT | 1020 |
| TTGAAGACCC | CACCAGACCT | GGGAAGCAGC | AACAGCTGGG | GCAGGAGCTG | AAGGAGCTGA | 1080 |
| TGAACACGGA | GCAGGCCTTG | GACCAGCTCA | TCCAGAGCTG | CTCTCTGAGC | TTCAAGCACC | 1140 |
| TGACTGAGGA | CAAGGCCAAC | AAGAGGCTGG | CCTATGTGAC | TTACCAGGAT | ATCCGTGCTG | 1200 |
| TTGGCAACTT | TAAGGAGCAG | ACAGTGATTG | CCGTCAAGGC | CCCTCCGCAG | ACGAGACTGG | 1260 |
| AAGTGCCCGA | CAGGACTGAG | GACAACCTGC | AGATATATCT | CAAGAGCACC | CAAGGGCCCA | 1320 |
| TCGAAGTCTA | CCTGTGCCCA | GAGGAGGTGC | AGGAGCCGGA | CAGTCCTTCC | GAGGAGCCTC | 1380 |
| TCCCCTCTAC | CTCCACCCTC | TGCCCCAGCC | CTGACTCTGC | CCAGCCCAGC | AGCAGCACCG | 1440 |
| ACCCTAGCAT | CATGGAGCCC | ACAGCATCCT | CAGTGCCAGC | ACCAGCGCCA | ACCCCCAGC | 1500 |
| AGGCCCCACC | GCCTCCATCC | CTGGTCCCCT | TGGAGGCTAC | TGACAGCCTG | CTGGAGCTGC | 1560 |
| CGCACCCACT | CCTGCAGCAG | ACTGAGGACC | AGTTCCTGTC | CCCGACCCTG | GCGTGCAGCT | 1620 |
| CCCCTCTGAT | CAGCTTCTCC | CCATCCTTGG | ACCAGGACGA | CTACCTGTGG | GGCTTGGAGG | 1680 |
| CGGGTGAGGG | CATCAGCGAT | CTCTTCGACT | CCTACGACCT | TGGGGACCTG | TTGATTAATT | 1740 |
| GAGTGGCCCT | GCCTGCCCCC | AGCAGCCTGC | CCCGACTCT | ACCTCCTCAC | AGACAGGCTG | 1800 |
| ACAGCCCCTC | TGCCTGCACA | GGGACATTGG | ACACTAGGTG | CTGCCCTCAG | GGCATGGGT | 1860 |
| CTCCTCGCCT | TTCCTGCCCC | AGCCGGCAGA | AGCTGTGTGG | GGAGATATGA | ATGGTACGGG | 1920 |
| TGAGGAGTGG | ATAAGGGGTG | GTCCTCACCT | TCCTAATGGA | AGCTGGGCCT | AGGGAGGCCC | 1980 |
| ATCCAGTCTT | CTGACTTCTG | ACCTCTCACA | AGAAGGCTGC | AGGTGAGGTG | GCCAAGTCCA | 2040 |
| GGGAAAGGCC | CTGCTACCTC | CTTTTGAGGG | GTAATTAGGA | CCCTCGACGT | ACCAAGAAGC | 2100 |
| ACATAATGCC | TTTGTATTTA | TTTCAGGTTG | AGTTGTTTGT | TTGTCCTCCC | TGAGTTTTAG | 2160 |
| CAGGGAGGTT | GTTCTAGTTT | TTAGTGAGAC | CTCTGCAGAC | AGGCCCATCA | CTGTCCATGT | 2220 |

```
TCCAGGGCAG  GTCTGGGTTT  CCAAGGGAGG  GGCCCAGGCT  ACATCCTTGG  TTTCCCCACT    2280

GTGGTGGGGG  CTGGGACTCT  GAGGGGCTGT  CCAGTCTGCT  AGAATGCTAA  TTGCACTTAG    2340

GCCTCATGGT  TCTAGTAAAC  GGCAGCTGTG  GGCCCTTTTG  CCTCTTCCCC  TGTTCTTGGC    2400

CTCACATCTC  CAGCTGAGCT  GCCGGTCTTG  GCTTCCTGGT  CGCCTCTGTC  CCAGAGATGG    2460

TCCCAGGGAG  CCATCCTAGG  GCAGGTAGCA  CTGAGGCTCC  TGTGGAAACA  GGAGCCACCT    2520

GCTCAGGAGA  CCCCTTTCCT  GAGGAAGTCC  TTACCTCTCC  CCTTGAGATG  TAAAAATGGT    2580

CCAGCAGAGA  CAAGCTCCCG  TGGAAAACAG  ACAGGAGCAT  GGGGGCAGCT  GTCATGGCTG    2640

TGGCGGG                                                                   2647
```

( 2 ) INFORMATION FOR SEQ ID NO:4:

( i ) SEQUENCE CHARACTERISTICS:
        ( A ) LENGTH: 437 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met  Ala  Leu  Ala  Gly  Ala  Pro  Ala  Gly  Gly  Pro  Cys  Ala  Pro  Ala  Leu
 1             5                        10                       15

Glu  Ala  Leu  Leu  Gly  Ala  Gly  Ala  Leu  Arg  Leu  Leu  Asp  Ser  Ser  Gln
               20                       25                       30

Ile  Val  Ile  Ile  Ser  Ala  Ala  Gln  Asp  Ala  Ser  Ala  Pro  Pro  Ala  Pro
          35                       40                       45

Thr  Gly  Pro  Ala  Ala  Pro  Ala  Ala  Gly  Pro  Cys  Asp  Pro  Asp  Leu  Leu
     50                       55                       60

Leu  Phe  Ala  Thr  Pro  Gln  Ala  Pro  Arg  Pro  Thr  Pro  Ser  Ala  Pro  Arg
65                       70                       75                       80

Pro  Ala  Leu  Gly  Arg  Pro  Pro  Val  Lys  Arg  Arg  Leu  Asp  Leu  Glu  Thr
                    85                       90                       95

Asp  His  Gln  Tyr  Leu  Ala  Glu  Ser  Ser  Gly  Pro  Ala  Arg  Gly  Arg  Gly
                    100                      105                      110

Arg  His  Pro  Gly  Lys  Gly  Val  Lys  Ser  Pro  Gly  Glu  Lys  Ser  Arg  Tyr
               115                      120                      125

Glu  Thr  Ser  Leu  Asn  Leu  Thr  Thr  Lys  Arg  Phe  Leu  Glu  Leu  Leu  Ser
     130                      135                      140

His  Ser  Ala  Asp  Gly  Val  Val  Asp  Leu  Asn  Trp  Ala  Ala  Glu  Val  Leu
145                      150                      155                      160

Lys  Val  Gln  Lys  Arg  Arg  Ile  Tyr  Asp  Ile  Thr  Asn  Val  Leu  Glu  Gly
                    165                      170                      175

Ile  Gln  Leu  Ile  Ala  Lys  Lys  Ser  Lys  Asn  His  Ile  Gln  Trp  Leu  Gly
               180                      185                      190

Ser  His  Thr  Thr  Val  Gly  Val  Gly  Gly  Arg  Leu  Glu  Gly  Leu  Thr  Gln
          195                      200                      205

Asp  Leu  Arg  Gln  Leu  Gln  Glu  Ser  Glu  Gln  Gln  Leu  Asp  His  Leu  Met
     210                      215                      220

Asn  Ile  Cys  Thr  Thr  Gln  Leu  Arg  Leu  Leu  Ser  Glu  Asp  Thr  Asp  Ser
225                      230                      235                      240

Gln  Arg  Leu  Ala  Tyr  Val  Thr  Cys  Gln  Asp  Leu  Arg  Ser  Ile  Ala  Asp
                    245                      250                      255

Pro  Ala  Glu  Gln  Met  Val  Met  Val  Ile  Lys  Ala  Pro  Pro  Glu  Thr  Gln
```

|       |       |       |       |       |       | 260   |       |       |       |       |       | 265   |       |       |       |       |       | 270   |       |       |
|-------|-------|-------|-------|-------|-------|-------|-------|-------|-------|-------|-------|-------|-------|-------|-------|-------|-------|-------|-------|-------|

```
            Leu  Gln  Ala  Val  Asp  Ser  Ser  Glu  Asn  Phe  Gln  Ile  Ser  Leu  Lys  Ser
                      275                      280                      285
            Lys  Gln  Gly  Pro  Ile  Asp  Val  Phe  Leu  Cys  Pro  Glu  Glu  Thr  Val  Gly
                 290                      295                      300
            Gly  Ile  Ser  Pro  Gly  Lys  Thr  Pro  Ser  Gln  Glu  Val  Thr  Ser  Glu  Glu
            305                      310                      315                      320
            Glu  Asn  Arg  Ala  Thr  Asp  Ser  Ala  Thr  Ile  Val  Ser  Pro  Pro  Pro  Ser
                                325                      330                      335
            Ser  Pro  Pro  Ser  Ser  Leu  Thr  Thr  Asp  Pro  Ser  Gln  Ser  Leu  Leu  Ser
                           340                      345                      350
            Leu  Glu  Gln  Glu  Pro  Leu  Leu  Ser  Arg  Met  Gly  Ser  Leu  Arg  Ala  Pro
                      355                      360                      365
            Val  Asp  Glu  Asp  Arg  Leu  Ser  Pro  Leu  Val  Ala  Ala  Asp  Ser  Leu  Leu
                 370                      375                      380
            Glu  His  Val  Arg  Glu  Asp  Phe  Ser  Gly  Leu  Leu  Pro  Glu  Glu  Phe  Ile
            385                      390                      395                      400
            Ser  Leu  Ser  Pro  Pro  His  Glu  Ala  Leu  Asp  Tyr  His  Phe  Gly  Leu  Glu
                                405                      410                      415
            Glu  Gly  Glu  Gly  Ile  Arg  Asp  Leu  Phe  Asp  Cys  Asp  Phe  Gly  Asp  Leu
                           420                      425                      430
            Thr  Pro  Leu  Asp  Phe
                           435
```

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CCAGGATCCC GGAGGCTGGA CCTGGAAACT G                31

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CCAGGATCCG GCAGAGGCCG CCATCCAGG                  29

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CCAGGATCCA CCTCACTGAA TCTGACCACC                  30

5,473,056

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CCAGGATCCG TCGTCGACCT GAACTGGGC                  29

( 2 ) INFORMATION FOR SEQ ID NO:9:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GCGGAATTCT ACAGCCACTG GATGTGGTTC TTGG             34

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GCGGAATTCT AGATGTCATA GATGCGCCGC TTC              33

( 2 ) INFORMATION FOR SEQ ID NO:11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GCGGAATTCT AGGTCTCATA GCGTGACTTC TC               32

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

CCAGGATCCA AATCCCCGG GGAGAAG                     27

( 2 ) INFORMATION FOR SEQ ID NO:13:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:13:

TAGTTTTCGA TATTAAATTT GAGTTTTCGC GCGAAACTAG      40

( 2 ) INFORMATION FOR SEQ ID NO:14:

( i ) SEQUENCE CHARACTERISTICS:
  ( A ) LENGTH: 12 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:14:

TTTCGATCCA AA      12

( 2 ) INFORMATION FOR SEQ ID NO:15:

( i ) SEQUENCE CHARACTERISTICS:
  ( A ) LENGTH: 42 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:15:

CCAAGGATCC ATTGGAGGAT GATTAAATGC TGCAAGGGCC CC      42

( 2 ) INFORMATION FOR SEQ ID NO:16:

( i ) SEQUENCE CHARACTERISTICS:
  ( A ) LENGTH: 44 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:16:

GAGAGCAAGC TTAGAACTCC TCATTAATCA ACAGGTCCCC AAGG      44

( 2 ) INFORMATION FOR SEQ ID NO:17:

( i ) SEQUENCE CHARACTERISTICS:
  ( A ) LENGTH: 47 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:17:

CCAGAGGATC CATTGGAGGA TGATTAAATG GCCTTGGCCG GGGCCCC      47

( 2 ) INFORMATION FOR SEQ ID NO:18:

( i ) SEQUENCE CHARACTERISTICS:
  ( A ) LENGTH: 46 base pairs
  ( B ) TYPE: nucleic acid
  ( C ) STRANDEDNESS: single (D) TOPOLOGY: linear (ii) MOLECULE TYPE: cDNA (xi) SEQUENCE DESCRIPTION: SEQ ID NO:18:

GAGAGCAAGC TTCTAGAACT CCTCGAAATC CAGGGGGGTG AGGTCC  46

(2) INFORMATION FOR SEQ ID NO:19:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GATCCATGCT GCAAGGGCCC CGGGCCTTGG CTTC  34

(2) INFORMATION FOR SEQ ID NO:20:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GGCCGAAGCC AAGGCCCGGG GCCCTTGCAG CATG  34

(2) INFORMATION FOR SEQ ID NO:21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

CCAGGATCCA AAAGGAAGCT GGATCTGGAG G  31

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

CCAGGATCCG TGGATGGCCT CCCCAGC  27

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA 5,473,056

33

34

-continued ( x i ) SEQUENCE DESCRIPTION: SEQ ID NO:23:

CCAGGATCCA AATCCCCCGG GGAGAAG 27

( 2 ) INFORMATION FOR SEQ ID NO:24:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

CCAGGATCCA CTTCGCTGGG GCTGCTCAC 29

( 2 ) INFORMATION FOR SEQ ID NO:25:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

CCAGGATCCG TCCTGGACCT GAACTGGG 28

( 2 ) INFORMATION FOR SEQ ID NO:26:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

GCGGAATTCT ATACCCACTG GATGTTGTTC TTGGC 35

( 2 ) INFORMATION FOR SEQ ID NO:27:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

GCGGAATTCA GTTGGCCTTG TCCTCAGTC 29

( 2 ) INFORMATION FOR SEQ ID NO:28:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

GGACGGATCC GACGACTACC TGTGGGGCTT G 31

( 2 ) INFORMATION FOR SEQ ID NO:29:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

CCTCGAATTC AGTCGAAGAG ATCGCTGATG CC    32